United States Patent [19]

Hewitt et al.

[11] Patent Number: 5,540,931
[45] Date of Patent: Jul. 30, 1996

[54] METHODS FOR INDUCING SITE-SPECIFIC IMMUNOSUPPRESSION AND COMPOSITIONS OF SITE SPECIFIC IMMUNOSUPPRESSANTS

[75] Inventors: Charles W. Hewitt, 698 Tranquility Turn, Marlton, N.J. 08053; Kirby S. Black, 13401 Sussex Pl., Santa Ana, Calif. 92705

[73] Assignees: Charles W. Hewitt, Marlton, N.J.; Kirby S. Black, Acworth, Ga.

[21] Appl. No.: 265,471

[22] Filed: Jun. 24, 1994

Related U.S. Application Data

[63] Continuation-in-part of Ser. No. 879,889, May 7, 1992, abandoned, which is a continuation of Ser. No. 637,056, Jan. 3, 1991, abandoned, which is a division of Ser. No. 318,676, Mar. 3, 1989, Pat. No. 4,996,193.

[51] Int. Cl.⁶ .................................... A61K 38/13
[52] U.S. Cl. .................... 424/434; 424/435; 424/436; 424/449; 514/9; 514/11; 514/43; 514/252; 514/258; 514/291; 514/323; 514/368; 514/614
[58] Field of Search ...................... 424/435, 427, 424/434, 449; 514/9, 11, 43, 252, 258, 291, 323, 368, 614

[56] References Cited

U.S. PATENT DOCUMENTS

| | | | |
|---|---|---|---|
| 3,288,824 | 11/1966 | Mahier et al. | 260/410.6 |
| 4,108,985 | 8/1978 | Ruegger et al. | 514/11 |
| 4,117,118 | 9/1978 | Harri et al. | 514/11 |
| 4,210,581 | 7/1980 | Ruegger et al. | 530/321 |
| 4,220,641 | 9/1980 | Traber et al. | 514/11 |
| 4,288,431 | 9/1981 | Traber et al. | 514/11 |
| 4,289,851 | 9/1981 | Traber et al. | 435/71.1 |
| 4,384,996 | 5/1983 | Bollinger et al. | 530/321 |
| 4,388,307 | 6/1983 | Cavanak | 514/11 |
| 4,396,542 | 8/1983 | Wenger | 530/321 |
| 4,553,974 | 11/1985 | Dewanjee | 8/94.11 |

(List continued on next page.)

FOREIGN PATENT DOCUMENTS

| | | |
|---|---|---|
| 0296122 | 12/1988 | European Pat. Off. . |
| 2638089 | 10/1989 | France . |
| 62-2019513 | 1/1987 | Japan . |
| 62-2019512 | 1/1987 | Japan . |
| 2207678 | 2/1989 | United Kingdom . |
| 3915617 | 5/1989 | United Kingdom . |
| 8901772 | 3/1989 | WIPO . |

OTHER PUBLICATIONS

Hewitt, et al. Transplantation 43: 13 (1988).
Hess, et al. Transplantation Proc. 20: 29 (1988).
Ellis, et al. Jama 256: 3110 (1986).
Toledo–Pereyra, et al. Transplantation 33: 330 (1982).
Aldridge, et al. Clin. Exp. Immunol. 59: 23 (1985).
Lai, et al. Transplantation 44: 83 (1987).
Zhao, et al. Transplantation Proc. 20: 670 (1988).
Towpik, et al. Transplantation 40: 714 (1985).
Biren, et al. J. Invest. Dermatol. 86: 611 (1986).

(List continued on next page.)

*Primary Examiner*—Gollamudi S. Kishore
*Attorney, Agent, or Firm*—Robbins, Berliner & Carson

[57] ABSTRACT

The present invention provides methods and formulations for site-specific immune suppression of immune/inflammatory responses with localized or topical application of immunosuppressants including cyclosporines, rapamycins (RPM), or combinations of immunosuppressants and anti-inflammatory compounds. Methods for the use of said formulations to effect site-specific immune suppression of local inflammatory/immune responses in mammalian tissue and for treatment of autoimmune, T-cell mediated immune disease, inflammatory conditions, inhibition of contact hypersensitivity, and for producing prolonged skin allograft survival, and wound healing are presented. In addition, methods for use of said formulations—in tandem with systemic applications of immunosuppressant such as cyclosporine or without same—are presented. The present invention also relates to alternative formulations and delivery systems for the efficacious treatment of the aforementioned conditions.

9 Claims, 18 Drawing Sheets

U.S. PATENT DOCUMENTS

| | | | |
|---|---|---|---|
| 4,554,351 | 11/1985 | Wenger | 544/177 |
| 4,639,434 | 1/1987 | Wenger et al. | 514/11 |
| 4,649,047 | 3/1987 | Kaswan | 514/11 |
| 4,677,968 | 7/1987 | Krueger | 128/898 |
| 4,681,754 | 7/1987 | Siegl | 514/1 |
| 4,703,033 | 10/1987 | Seebach | 514/11 |
| 4,764,503 | 8/1988 | Wenger | 514/11 |
| 4,771,122 | 9/1988 | Seebach | 530/317 |
| 4,839,342 | 6/1989 | Kaswan | 514/11 |
| 4,857,662 | 8/1989 | Satzinger et al. | 564/168 |
| 5,059,611 | 10/1991 | Lee | 514/336 |
| 5,124,392 | 6/1992 | Robertson | 424/427 |

OTHER PUBLICATIONS

Ried, et al. Transplantation Proc. 15: 2434 (1983).
Thivolet, et al. Lancet 1: 334 (1985).
Harper, et al. Lancet 2: 981 (1984).
Thomson, et al. Lancet 1: 1212 (1987).
Mosteller, et al. Arch Ophthalmol 103: 101 (1985).
Levinger, et al. J. Med. Sci 21: 670 (1985).
Shuster, S. Transplanatation Proc. 20: 19 (1988).
Black, et al. Transplantation Proc. 20(2): 660–662 (1988).
Biren, et al. Arch Dermantol. 122: 1028 (1986).
Aldridge, et al. Lancet 1: 160 (1985).
Mueller, et al. NEJM 301: 555 (1979).
Eisen, et al. NEJM 323(5): 290–294 (1990).
Wenger, et al. Pharmacol. Rev 41: 243–247 (1989).
Nakagawa, et al. Chem. Abst. 109: 48022e (1988).
Newton, et al. Chem. Abst. 108: 118879v (1988).
Hunter, et al. Chem Abst. 95: 73790d (1981).
Bousema, et al. J. Am. Acad. Dermat 22(1): 126–127 (1990).
Duncan, et al. British J. of Dermat 123: 631–640 (1990).
Griffiths, et al. The Lancet: 1212 (1987).
Gupta, et al. J. Invest. Dermat 93(3): 379–386 (1989).
Lai, et al. Surg. Forum 37: 603–604 (1986).
Nakagawa, et al. Arch Dermatol. 124: 907–910 (1988).
Stokar, et al. Res. Commun. in Pathology & Pharmacology 68(1): 117–120 (1990).
Yokoo, et al. Arch Dermatol. Res. 282: 408–411 (1990).
Zhao in Transplantation proceeding XX#2, 1988, p. 670.

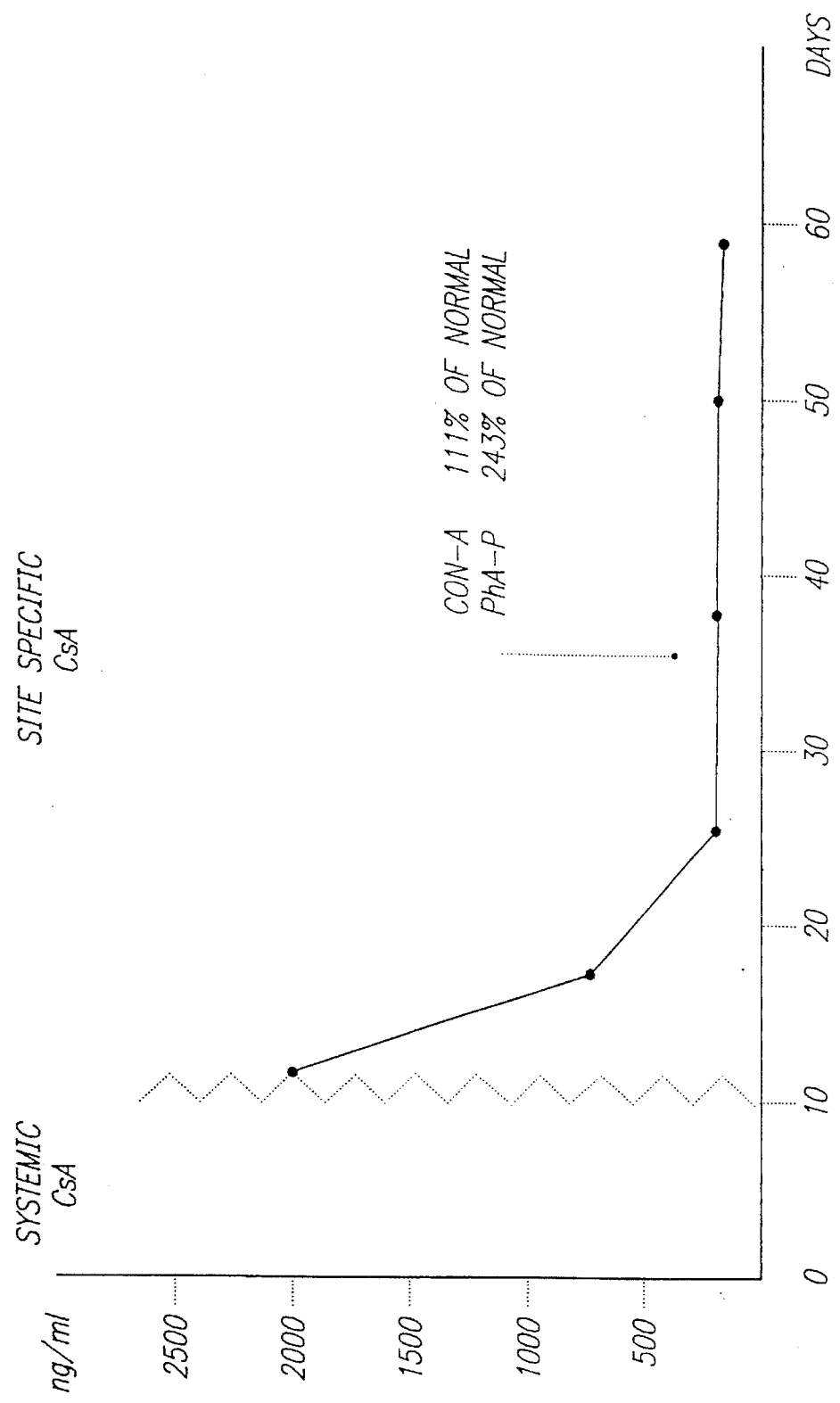

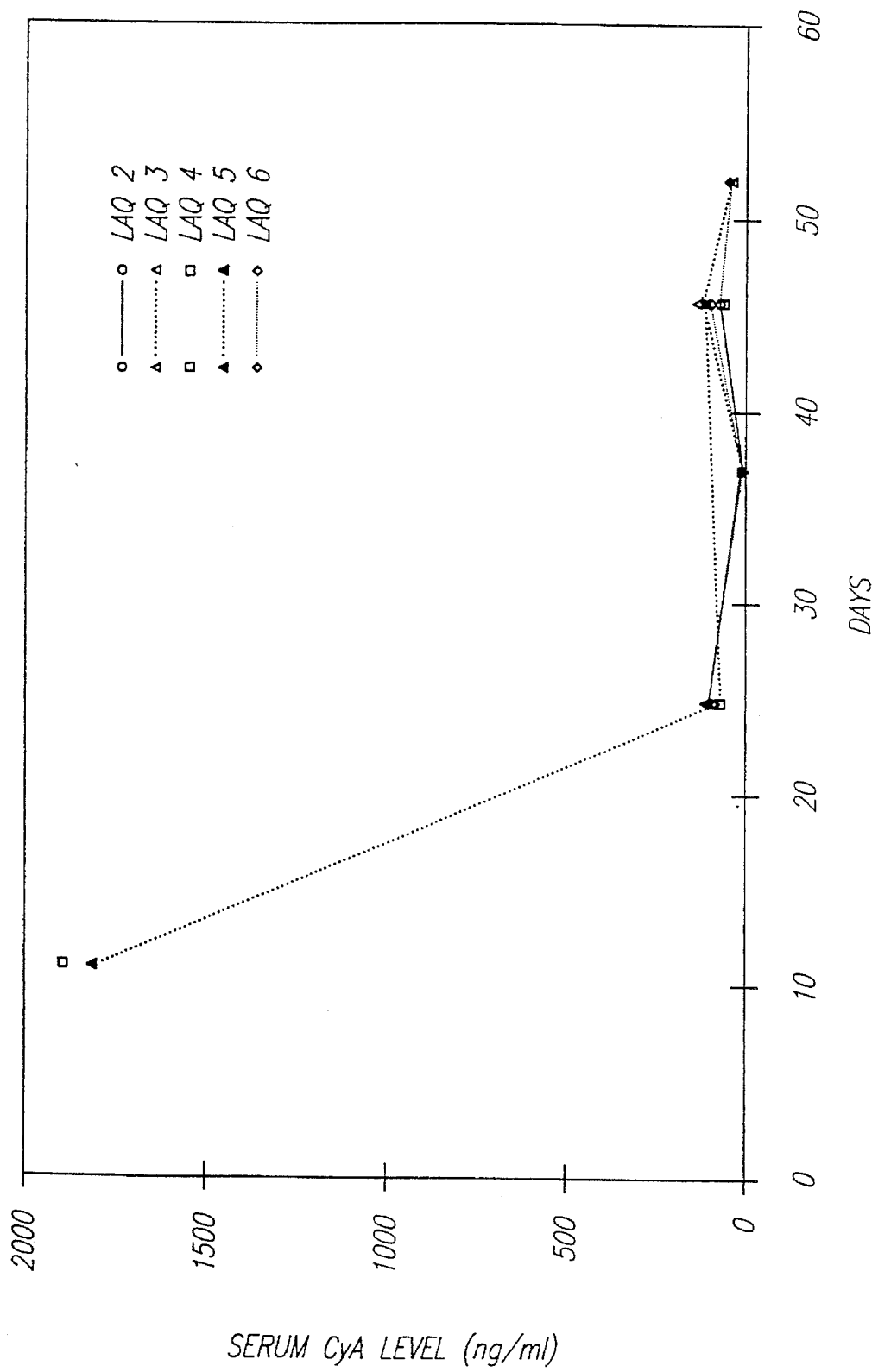

LAQQ 1-8
AVERAGE CyA LEVEL WITH 95% CONFIDENCE INTERVAL
USING SPECIFIC AND NON-SPECIFIC DATA

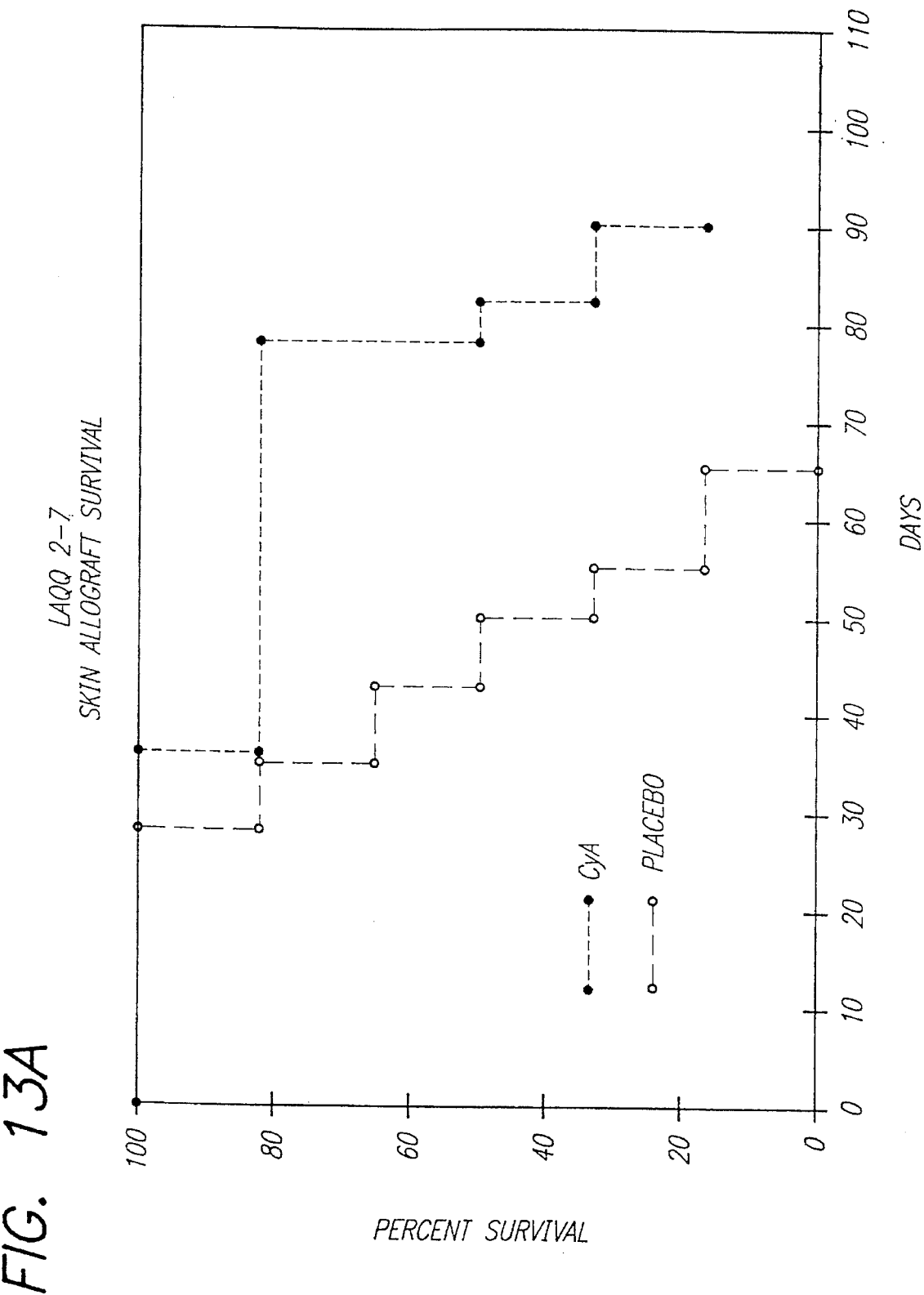

METHODS FOR INDUCING SITE-SPECIFIC IMMUNOSUPPRESSION AND COMPOSITIONS OF SITE SPECIFIC IMMUNOSUPPRESSANTS

BACKGROUND OF THE INVENTION

This is a continuation-in-part of Ser. No. 07/879,889 filed May 7, 1992, now abandoned which is a continuation of Ser. No. 07/637,056, filed Jan. 3, 1991, now abandoned, which is a divisional of Ser. No. 07/318,676, filed Mar. 3, 1989, now U.S. Pat. No. 4,996,193, which issued on Feb. 26, 1991.

Cyclosporine (CsA), a selective immunosuppressant and a potent anti-inflammatory agent, has demonstrated great clinical success in inhibiting T-cell mediated immune processes such as allograft rejection, graft-versus-host disease, and autoimmune disease when administered systemically. (See, e.g., A. D. Hess al., *Transpl. Proc.* 20: 29 (1988).) As to the latter, systemic CsA has been proven efficacious for treating psoriasis, an autoimmune disorder of the skin. (See, e.g., C. N. Ellis, et al., *JAMA* 256: 3110 (1986).). However, the induction of immunosuppression at the tissue site and focal responding immunocytes could result in surprisingly greater efficacy, and could have significant immunologic and clinical ramifications.

As an example of the aforementioned ramifications, within the specialty of dermatology, it would be desirable to treat putative autoimmune conditions and related diseases of the skin, including, for example, eczema, contact hypersensitivity, alopecia areata and psoriasis. Few if any models for testing the disease mechanism and the efficacy of various treatment modalities have been available in this field, however. Moreover, due to the variability of expression of most skin conditions, and the inherent differences between epidermal tissues in various locations on the body, a single treatment methodology or pharmaceutical composition is rarely effective for all disease conditions presented.

A basic understanding of the immune response involved will facilitate the understanding and appreciation of the present invention. T-cell mediated immune events play an important role in eliciting allograft rejection and other inflammatory reactions. The immunological cascade that follows alloengraftment includes: (1) recognition of antigen; (2) lymphocyte activation; (3) development of specific cellular and molecular lines of communication between responding immunocytes via lymphokine release and induced expression of major histocompatibility complex ("MHC") antigens; and (4) mononuclear inflammatory cell infiltration into the target tissue which leads to eventual graft destruction (rejection). Systemic administration of CsA, a novel fungal metabolite, is well known to block this inflammatory cascade and to facilitate permanent allograft acceptance (actively-acquired immunological tolerance) in various experimental animal models, probably by inhibitory effects upon T-helper cells with sparing of T-suppressor cell expression. (See, e.g., A. D. Hess, et al., *Transpl. Proc.* 29 (1988).) Cyclosporines and other similar immunosuppressants such as rapamycins, FK-506 derivatives and immunophilin binding agent have novel immunosuppressive properties compared to conventional agents: they are selective in their mechanism of action, demonstrate superior graft survival times, and are potent anti-inflammatory compounds. Cyclosporines are well-recognized for their powerful ability to permanently alter immune responsiveness, in comparison with conventional agents, so that some degree of selective immunologic tolerance (graft acceptance) can be achieved in various models. Therefore, it would be extremely advantageous and desirable to develop topical formulations of cyclosporines, rapamycins and other immunosuppressants for localized tissue site-specific action.

Conventionally, immunosuppressants have been administered at a systemic level in order to inhibit both cell- and humoral-mediated immune responses. However, the induction of localized site-specific immunosuppression could inhibit the mechanisms which lead to graft rejection and similar inflammatory immune processes operative in autoimmune and putative autoimmune disorders. Yet, a tissue site-specific immunosuppressive mechanism has not been conclusively demonstrated by local application of the cyclosporines.

More recently, the fungal metabolites known as cyclosporines, and particularly Cyclosporine A (CsA), have been established as the principal immunosuppressants in solid organ transplantations. The systemic use of cyclosporine prolongs the survival of experimental and clinical allografts, but continuing immunosuppressive therapy is generally necessary.

Yet, the long-term side effects of systemic administration of cyclosporines and other immunosuppressants are of major concern. The related complications of nephrotoxicity and hepatotoxicity (i.e., kidney and liver damage), as well as an increase in infections, are a significant problem and may thus render treatment with cyclosporines inappropriate for certain patients, such as those who have been severely burned, or for those with skin conditions that are not life-threatening, such as psoriasis. One method for achieving indefinite survival of the graft or prolonged anti-inflammatory effects with CsA and/or other immunosuppressants and for reducing potentially toxic systemic side effects involves the localization of CsA and/or other immunosuppressants in the target tissue.

For the purposes of clarity and easier comprehension, the terms "CsA", "Cyclosporine A" and "cyclosporine" may be considered interchangeable with the term "cyclosporin(s)" throughout this disclosure. While CsA is the cyclosporine typically used in most pharmaceutical preparations, the scope of this invention is not limited to this one type of cyclosporine. Likewise, the terms "rapamycin", "RAP", "RPM", "rapamycin derivatives", and "rapamycin pro-drugs" may be considered interchangeable with the term "rapamycin(s)" throughout this disclosure. Similarly, the terms "steroid", "anti-inflammatory hormone", "corticosteroid anti-inflammatory", "corticosteroid", "glucocorticoid anti-inflammatory", "glucocorticoid", "steroid anti-inflammatory" and "steroid immunosuppressant" may be considered interchangeable throughout this disclosure.

Local inhibition of the rejection response with CsA has demonstrated mixed results. Perfusion of kidney allografts with CsA prior to transplantation did produce enhancement of tissue survival; however, prior, minimal systemic azathioprine immunosuppression was required. See, e.g., L. H. Toledo-Pereyra, et al., *Transplantation* 33:330 (1982). Likewise, infusion of low-dose CsA into the ligated thoracic duct provided only a mild enhancement of rat kidney allograft survival. Delayed type hypersensitivity has been effectively inhibited in animals and man with topically-applied CsA (see, e.g., R. D. Aldridge, et al., *Clin. Exp. Immunol.* 59: 23, 1985), as has cornea allograft rejection. The topical application of CsA has also been shown to be effective in treating alopecia areata and contact hypersensitivity in humans, yet it appears to have no effect on psoriasis. Studies using topically-applied CsA demonstrated prolonged survival of rat skin allografts; see, e.g., C. S. Lai, et al., *Transplantation* 44: 83, 1987, X. F. Zhao, et al., *Transplant. Proc.* 20: 670 (1988). However, one such study concluded that most of the enhancement observed with local CsA treatment was due to the animals' ingestion of CsA from the treated area. See Zhao, supra. When means were taken to prevent the animals from ingesting CsA from the grafts, the investigators found that CsA blood levels were suboptimal (below 100 ng/ml) and negligible enhancement of skin allograft survival was seen. It has also been postulated that autoimmune disorders of the skin could benefit from transdermal (i.e., localized) treatment with CsA.

Thus, there is a need for topical and local formulations of immunosuppressants, particularly those that react with immunophilin cytosolic binding proteins, which include but are not limited to cyclosporines, rapamycins, FK 506 derivatives and prodrugs, and combinational immunosuppressants. There is also a need for a method for utilizing same, in the prevention of localized tissue site-specific inflammatory immune reactions. An example includes prevention of skin allograft rejection and contact hypersensitivity reactions at a local level, but these would serve as models for other inflammatory disorders such as autoimmune disease of the skin (i.e., psoriasis, lupus, contact hypersensitivity, alopecia areata, dermatitis, dermatoses), localized tissue auto- or allo-inflammatory/immune responses, and tissue or organ allografts. In particular, a methodology that locally provides allograft acceptance and attenuates T-cell mediated events is highly desirable. The present invention is directed to such formulations and methods of use.

Immunosuppressants represent a revolutionary new class of potent anti-inflammatory agents possessing selective actions and reduced side-effects. Their mechanism of action is not completely known. However, such immunosuppressants derived from microorganisms including the cyclosporines, and macrolides such as FK506, Rapamycin and derivatives possess common properties. They are lipophilic antibiotics that inhibit the transcription of T cell activation genes and/or signal transduction pathways involved in T cell activation. A class of cytosolic binding proteins for these agents have been identified (immunophilins), which are peptidyl-prolyl-cis- trans-isomerases and have been implicated in signaling pathways for T cell activation.

The status of the immune system must be considered as either activated (primed) or inactivated (resting). Some immunosuppressive compounds may preferentially affect immune mechanisms in the resting state to inhibit progressive activation. However, other agents may be at a disadvantage in inhibiting a preactivated immune response. Cyclosporine has been shown to provide potent and selective immunosuppression in the preactivation phase of in vitro and in vivo models. A prominent mechanism of action for cyclosporine and other similar immunosuppressants is inhibition at the level of the CD4+ MHC class II responsive helper T cell. In particular, cyclosporine inhibits the release of cytokines such as IL-2 and allows expression of antigen specific suppressor circuits.

One of the most fascinating and important aspects of the cyclosporines and other immunosuppressants is that they are well-known to induce some degree of permanent attenuation of immune responsiveness. This is known as induction of immunological tolerance. Research in our laboratories and others have supported this conclusion. This fact alone makes cyclosporine an exciting and novel candidate drug for autoimmune and inflammatory diseases along with other similar immunosuppressants.

Yet, systemic immunosuppressant administration is of great concern due to dangerous unwanted side-effects. Thus, it would be extremely advantageous to effect site-specific immunosuppression with the cyclosporines or other similar immunosuppressants by targeting the drug to specific tissue sites. Targeting the drug to the site where it is most needed would help overcome this concern and increase efficacy. However, the cyclosporines are generally known to be primarily effective only during induction of immune responsiveness, not following activation of immunity. Therefore, due to the known mechanisms of action for these novel immunosuppressants, it would not necessarily be hypothesized that such agents could be effective in autoimmune disease states where activation is already occurring. Yet, most surprisingly, and in contradistinction to these known mechanisms, we have demonstrated that dramatic site-specific efficacy can indeed be achieved with cyclosporine using site-specific application.

Specifically, new research has proven that inflammatory reactions in the skin can be inhibited at the tissue site using topical formulations of immunosuppressants. Details concerning topical drug formulations and the critical methodology for their successful use are provided herein. The basic technology of site-specific immunosuppression involves: the physicochemical properties of immunosuppressants related to drug delivery and targeting to specific tissue sites; and immune principles discovered that are necessary for inhibiting activated immune responses by cyclosporine, rapamycin, and other immunosuppressants during a disease state.

SUMMARY OF THE INVENTION

The present invention exploits observations that: 1) cyclosporine and rapamycin inhibit primary inflammatory/immune responses by local application using in vitro cellular site-specific models; 2) cyclosporine and rapamycin inhibit activated inflammatory/immune responses by local application using in vitro cellular site-specific models; 3) rapamycin is surprisingly efficacious with local application during both late and early inflammatory immune phases using in vitro cellular site-specific models; 4) cyclosporine is more efficacious locally during the early inflammatory immune phase compared to the late phase using in vitro cellular site-specific models; 5) consistent with these in vitro findings, either cyclosporine or rapamycin inhibit local inflammatory/immune responses by topical application to skin tissue using in vivo models of site-specific immune suppression; 6) this includes site-specific immune suppression effected by topical use of cyclosporine and rapamycin combinations in contact hypersensitivity reactions of skin tissue; 7) rapamycin is particularly efficacious during the late local inflammatory-immune phase in this latter example; 8) cyclosporine is particularly efficacious during the early local inflammatory immune phase in this latter example; and 9) in agreement with these results, skin allograft survival may be prolonged via topical use of cyclosporines, alone and in combination with other anti-inflammatory agents, and more particularly, with Cyclosporine A alone or combined with steroidal anti-inflammatory agents such as hydrocortisone to produce synergistic results.

The present invention is based on the concept that targeting CsA, RPM, other immunosuppressants, or combinations of immunosuppressants and anti-inflammatory compounds to a specific tissue is a desirable means for increasing efficacy and reducing systemic toxic concerns associated with these immunosuppressants. This localized effect of immunosuppressants also indicates potential usefulness in organ transplants, via perfusion and/or topical application. Further, immunosuppressants may be effective in the clinical treatment of autoimmune skin disorders and other localized inflammatory reactions. In general, then, this treatment may be appropriate whenever there is a T-cell-mediated or mononuclear cellular inflammatory reaction incited by a fixed-tissue-based antigen and/or unknown mechanisms. In addition, local application with cyclosporines, RPM, immunosuppressants, or combinations of immunosuppressants and additional anti-inflammatory agents may prove efficacious for the treatment of rheumatoid arthritis, osteoarthritis, temporal-mandibular joint disease (TMJ), asthma, multiple sclerosis, colitis, ophthalmic inflammatory conditions, uveitis, meningitis, inflammatory bowel disease, myositis, inflammation of oral and esophageal tissues, inflammatory lung disease, inflammation associated with myocardial infarction and cerebral vascular disease or accidents, trauma induced inflammation, and other inflammatory/immune disorders.

A critical mechanism for the induction of site-specific immune suppression by immunosuppressants appears to be the establishment of a systemic maintenance phase of immune nonresponsiveness. To induce this maintenance state, an initial limited systemic dose of CsA or another immunosuppressant appears necessary. Analogously, it is well-recognized that two distinct states of immunosuppression, the induction and maintenance phases, are important for the development of specific immune non-responsiveness. (See, e.g., E. Towpik, et al., *Transplantation* 40: 714 [1985]). It is not unlikely that immunosuppressant, dosing requirements for efficacious site-specific suppression of autoimmune inflammatory skin disorders will underscore this observation. Either continuous or limited low-dose immunosuppressant administered systemically at various times in conjunction with topical application may also prove efficacious. Additionally, transdermal delivery of immunosuppressants thereby providing systemic and local effects may also prove efficacious.

In accordance with one aspect of the present invention, there is provided a method for utilizing local CsA, in a topical formulation in conjunction with a short-term, limited systemic CsA schedule or a longer-term, low-dose systemic CsA schedule for effective abrogation of skin allograft rejection, T-cell mediated immune processes, and inflammatory reactions. This method should also prove effective in the clinical treatment of autoimmune skin disorders including psoriasis and other localized inflammatory reactions or cyclosporine-responsive conditions. One preferred embodiment suggests a-systemically applied formulation wherein about 1 mg/kg/day to 25 mg/kg/day of cyclosporine is applied per single dosage.

In accordance with another aspect of the present invention, there is provided a method for utilizing local CsA in combination with additional anti-inflammatory agents, such as steroids or hydrocortisone, in a topical formulation for synergistic abrogation of skin allograft rejection, T-cell mediated immune processes, and inflammatory reactions. This method should also prove effective in the clinical treatment of autoimmune skin disorders including psoriasis and other localized inflammatory reactions or immunosuppressant-responsive conditions.

In accordance with another aspect of the present invention, there is provided a method for utilizing local rapamycin in a topical formulation for efficacious abrogation of skin hypersensitivity reactions, T-cell mediated immune processes, and inflammatory reactions. This method should also prove effective in the clinical treatment of autoimmune skin disorders including psoriasis and other localized inflammatory reactions or immunosuppressant-responsive conditions.

In accordance with another aspect of the present invention, there is provided a method for utilizing local CsA in combination with a immunosuppressant agent, rapamycin, in a topical formulation for efficacious abrogation of skin hypersensitivity reactions, T-cell mediated immune processes, and inflammatory reactions. Novel combinations of immunosuppressive agents such as rapamycin and cyclosporine enable differential actions on immunoactivation pathways for potential synergism. This method should also prove effective in the clinical treatment of autoimmune skin disorders including psoriasis and other localized inflammatory reactions or immunosuppressant-responsive conditions.

In one embodiment, CsA is suspended in a topical cream formulation of a particular composition. In another embodiment, CsA is a component of a mineral oil-based topical formulation of a particular composition. In accordance with yet another embodiment of the invention, a topical formulation of cyclosporine is provided wherein CsA is embodied in a jojoba oil-based topical formulation of a particular composition. In accordance with other embodiments, the formulation is embodied in a paste, a gel, a liquid or a spray. Additionally, other embodiments include topical formulation of CsA in conjunction with different immunosuppressants and anti-inflammatory agents. Additional embodiments include formulations containing a preservative, as well.

For example, one preferred type of formulation according to the present invention may generally comprise cyclosporine, a pharmaceutical carrier, a co-solvent, a penetration enhancer, and an emulsifier. In a further embodiment, said components may be present in these approximate quantities: 5–80% pharmaceutical carrier; 5–50% co-solvent; 1–5% penetration enhancer; 0.1–20% emulsifier; and 0.2–25% cyclosporine (or cyclosporine applied to the tissue in such an amount that from about 0.5 mg/cm$^2$ to 5 mg/cm$^2$ of cyclosporine is applied per single dose).

Another preferred type of formulation according to the present invention may generally comprise, in approximate amounts by weight, 5–60% anhydrous lanolin; 5–60% mineral oil; 5–60% olive oil; 5–30% ethyl alcohol; 5–50% deionized water; 5–15% glycerol; 0.2–20% polysorbate 80; 1–5% polyvinylpyrrolidone; 0.2–25% cyclosporine A powder; and 0.1–10% sodium dodecyl sulfate.

Still another preferred type of formulation according to the present invention may generally comprise, in approximate amounts by weight, 5–60% anhydrous lanolin; 5–80% jojoba oil; 5–80% olive oil, 0.2–20% polysorbate 80; and 0.2–25% cyclosporine A powder.

An additional preferred type of formulation according to the present invention may generally comprise, in approximate amounts by weight, 5–60% anhydrous lanolin; 5–80% white petrolatum; 5–80% olive oil; 0.2–20% polysorbate 80; and 0.2–25% cyclosporine A powder.

Another preferred type of formulation according to the present invention may generally comprise, in approximate amounts by weight, 5–60% anhydrous lanolin; 5–80% white petrolatum; 5–80% olive oil; 0.2–20% polysorbate 80; and 0.2–25% cyclosporine A powder.

Another preferred type of formulation according to the present invention may generally comprise, in approximate amounts by weight, 60–90% ethyl alcohol; 3–30% glycerol; 0.2–20% polysorbate 80, and 0.2–25% cyclosporine A powder.

According to the present invention, yet another example of a preferred formulation generally comprises, in approximate amounts by weight, 0–50% ethyl alcohol (v/v); 5–30% glycerol (v/v); 10–90% propylene glycol (v/v); and 0.2–25% cyclosporine A powder (w/v).

Another preferred type of formulation according to the present invention may generally comprise, in approximate amounts by weight, 0.2–20% polysorbate 80 (v/v); 2–30% ethyl alcohol (v/v); 5–50% deionized water (v/v); 5–40% glycerol (v/v); 10–80% propylene glycol (v/v); and 0.2–25% cyclosporine A powder (g/100 ml; w/v).

Another preferred type of formulation according to the present invention may generally comprise, in approximate amounts by weight, 0–20% ethanol (v/v); 0.2–25% cyclosporine (w/v); 19–80% white petrolatum (v/v); 0–10% heavy mineral oil (v/v); and 0.05–5% steroid powder (w/v). A further embodiment may utilize hydrocortisone as the steroid powder of choice.

Yet another preferred type of formulation according to the present invention may generally comprise cyclosporine and a pharmaceutically acceptable pharmaceutical carrier. Such a formulation may further comprise an esterification product of natural triglycerides and polyethylene glycol; a vegetable oil; and ethanol.

Another preferred type of formulation according to the present invention may generally comprise a formulation wherein the weight ratio of ester to cyclosporine is about 10:0.2 to 10 parts by weight; vegetable oil is about 35 to 60% of the total composition by weight; and ethanol is about 1 to 20% of the total composition by weight. Further, such a formulation may generally include cyclosporine, wherein the cyclosporine is cyclosporine A powder in a concentration by weight of about 0.5% to about 25%.

In accordance with another aspect of the present invention, a dual skin graft model is provided, which may be used, for example, to test treatment protocols, such as the tandem treatment method suggested herein, or the topical administration of various cyclosporine-containing formulations.

Further, the present invention proposes that the use of pharmaceutically acceptable co-solvents and potential penetration promoters in cyclosporine-containing topical treatment formulations that may result in decreased or lost efficacy locally, but increased efficacy systemically. Therefore, a gradient effect may be created by such formulations in the locally-treated tissues which extends into the systemic circulation. However, by lowering cyclosporine doses with such formulations, the potentially desired local result can be effected. In contradistinction, topical cyclosporine formulations without said co-solvents and obvious penetration promoters generally appear to facilitate deposition of the active agent locally in the treated tissues. These latter formulations are more effective at producing only localized effects without systemic involvement at equivalent cyclosporine concentrations.

In addition, it is suggested that various combinations of cyclosporines, steroids and other anti-inflammatory agents (non-steroidal agents, for example) be used in the local treatment of autoimmune and other inflammatory conditions to provide combined, additive, and/or synergistic efficacy.

In another embodiment of the present invention, alternative delivery systems, such as microencapsulation of cyclosporine-containing formulations within lipid membranous vesicles such as liposomes, or microemulsions are suggested.

Other embodiments of the present invention include the effective administration of CsA for systemic purposes via transdermal application. It is thought that this novel route of administration of CsA may provide new mechanisms of systemic action of CsA due to different metabolism when cyclosporine passes through the epidermis/dermis. These results also support the use of topical CsA formulations as an effective means for systemic delivery in patients needing immunosuppression but who may present compromised gastrointestinal absorption.

In addition, it is suggested, in another embodiment, that CsA may be administered locally to various tissues other than the skin; e.g., to the oral mucosa, the esophagus, the nasal septum, the bronchical tubes, and lung tissue, to name a few.

Moreover, CsA has been shown to have mild antifungal properties and topical application may be effective for fungal infections. Such application is suggested in another embodiment of the present invention.

Finally, the present invention proposes a method for utilizing any one of several topical CsA, RPM, combined CSA-RPM, combined immunosuppressant, or combined immunosuppressant/anti-inflammatory formulations in conjunction with systemically-applied CsA, or independently of same. Examples of substances which may be used as co-solvents in the illustrated embodiments include the following: ethanol; oleyl alcohol; alkylene polyols; glycerol; polyethylene glycol; oleic acids, vegetable oil PEG-6 complexes; caprylic triglyceride; capric triglyceride; glyceryl caprylate; glyceryl caprate; PEG-8 caprylate; PEG-8 caprate; ethoxydiglycol; and any mixture thereof.

Examples of substances which may be used as penetration enhancers in the illustrated formulations include the following: ethanol; oleyl alcohol; alkylene polyols; oleic acids; urea; pyrrolidones; surfactants such as sodium lauryl sulfate; vegetable oil PEG-6 complexes such as the commercially available Labrafils (Gattefosse, Elmsford, N.Y.); caprylic/capric triglyceride (i.e., Labrafac Hydro, Gattefosse); glyceryl caprylate/caprate and PEG-8 caprylate/caprate (Labrasol, Gattefosse); and ethoxydiglycol (i.e., Transcutol, Gattefosse) caprylic triglyceride, capric triglyceride; glyceryl caprylate; glyceryl caprate; PET-8 caprylate; PEG-8 caprate; and any mixture thereof.

One advantage of the present invention over the prior art includes the fact that topical application of cyclosporine is effective in abrogating skin allograft rejection, inflammatory reactions and autoimmune skin disorders, without interfering with other cellular processes. As noted previously, other topically-applied formulations, such as those containing steroids, exclusively are less efficacious immunosuppressants, are less selective in their actions, and are less effective at inducing permanent immunologic tolerance than are cyclosporines or similar immunosuppressants. Further, in the case of steroid creams and ointments used exclusively, a detrimental effect on wound healing and non-specific immunity against infection may result from their use.

A further advantage of the present invention is the fact that selectively delivering cyclosporine or immunosuppressant to a specific tissue targets the compound to responsive inflammatory cells and is a desirable means of increasing efficacy and reducing systemic toxic concerns associated with immunosuppressants, in that the localized effect of cyclosporine indicates that it is potentially useful in organ transplants via topical application and/or via perfusion. Topical application of cyclosporine promotes allograft survival by delivering the compound to the target tissue, which facilitates the site-specific activity and efficacy of this immunosuppressant, while reducing potentially toxic systemic levels of cyclosporine.

Another advantage of the present invention is the fact that the dual skin allograft model provides an excellent research and clinical study protocol. For example, use of two allografts, one receiving treatment and the other left untreated, allows in vivo assessment of the systemic T-cell mediated response against the particular allograft in question. Since the treated allograft will potentially elicit systemic alloactivation, assessment of the test substance's ability to locally suppress these systemic alloaggressive cells will be possible. In addition, local effects of a test substance may be studied via the proposed dual skin allograft model.

Further advantages include the efficacy of the invention in treating a disease such as alopecia, where relatively normal skin is receiving treatment. In such instances, the required formulation is likely to be different from that which would effectively treat a more severe skin disorder such as psoriasis complicated by open lesions. In addition, dose and timing requirements will require study of the patient by the practitioner, and may necessitate variations for both systemic and topical phases of treatment with immunosuppressants.

Likewise, some conditions may require topical immunosuppressant application alone, without prior systemic CsA treatment. Moreover, different formulations may easily be devised according to the protocols and methods set forth herein, to produce creams or ointments which may prove efficacious and advantageous.

Experiments confirm that there are two important aspects which must be considered when investigating local immunosuppressive therapy: immune function and pharmacology. Data discussed below deals exclusively with either 1) local interference of immune and inflammatory activation mechanisms (immune function); 2) pharmacology of local immunosuppressant delivery to specific tissue sites by topical application; or 3) combined immune functional and pharmacologic considerations.

Immunology of Site-specific Immune Suppression

One can assume in autoimmune and inflammatory diseases there exists a state of immune activation. Under these conditions cyclosporine may theoretically be limited to therapy in disease states consistent with known mechanisms of cyclosporine immunosuppression where immune activation is being initiated. However, both in vitro and in vivo data within our lab demonstrates that CsA does indeed have potent immunosuppressive effects on preactivated cells, as concentrations are increased to relatively high values locally (see FIG. 1 A, B and C).

Figure 2:
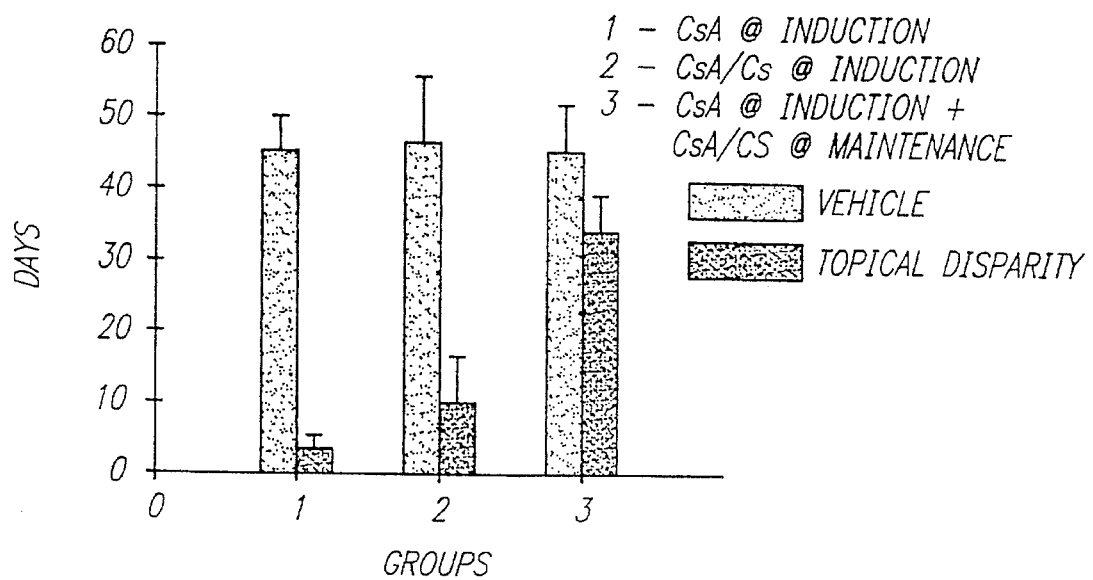
FIG. 2 shows synergistic mean disparity in dual skin allograft survival with combined topical application of CsA and steroid.
Figure 3:
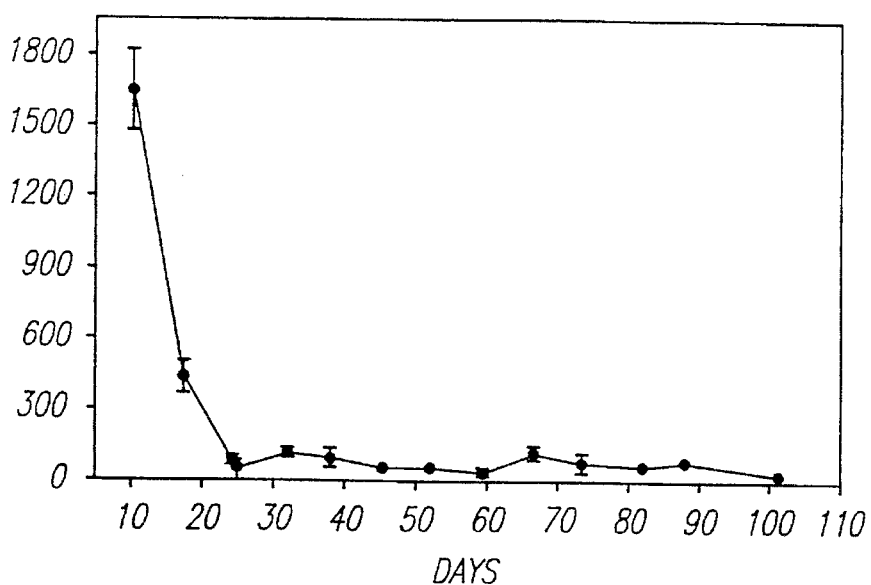
FIG. 3 shows systemic serum CsA concentrations over time in graft recipients of FIG. 2.

In FIG. 2, topical CsA provided moderate graft prolongation and disparity in a vehicle system that provided less-than-optimal transepidermal delivery and graft prolongation and was designed to test for combinational immunosuppressant synergism (Bar 1). Mean survival times increased slightly with combined topical CsA/HC in comparison to CsA alone, but, did not provide a significant synergism (Bar 2). However, topical CsA during immune response induction or the antigen-dependent phase with subsequent suppression of antigen-independent inflammation by topical CsA/HC provided dramatic synergism with optimal efficacy and disparity (Bar 3). In FIG. 3, systemic profiles of serum CsA yielded a predictable trend in placebo treated skin allograft survival. Ten day subcutaneous treatment reached a peak of 1,700 ng/ml at day 11. Subtherapeutic levels were reached and maintained by day 25. Placebo grafts rejected shortly thereafter.

High CsA levels in the systemic circulation would normally be expected to produce organ toxicity. However, high levels of CSA can be localized at the tissue site undergoing immune activation without adverse effects (see test systems below and FIG. 4).

Figure 4:
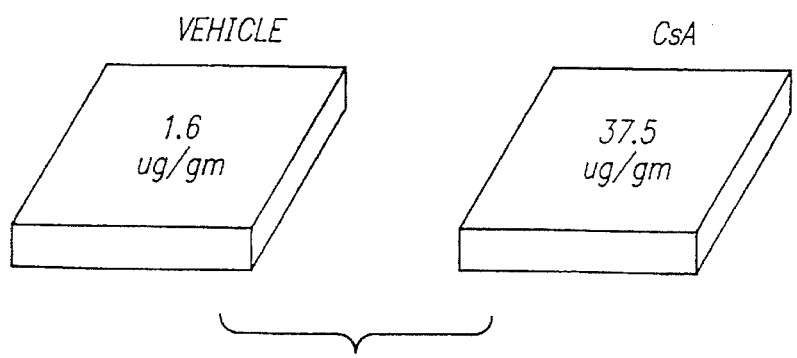
FIG. 4 shows site-specific immunosuppressant delivery as measured by local cyclosporine tissue concentrations.
Figure 5:
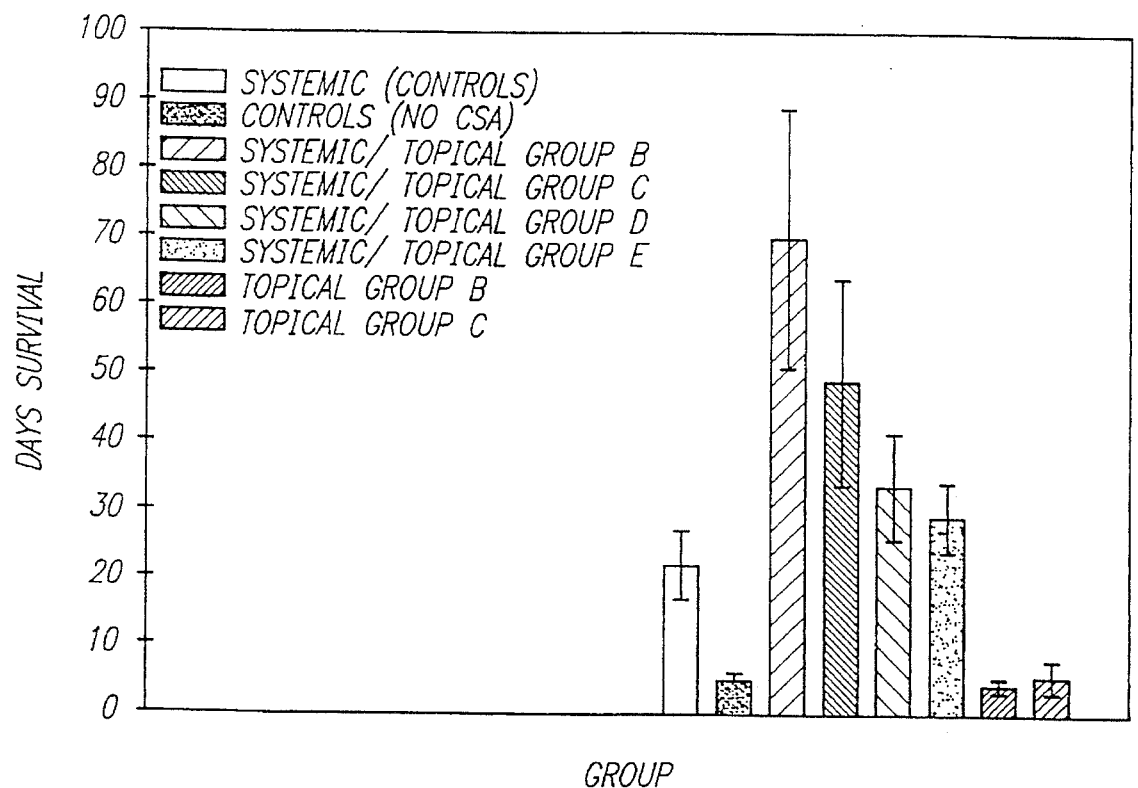
FIG. 5 shows optimal site-specific immune effects are achieved by prior limited systemic immunosuppressant treatment with CsA.

In FIG. 4, the skin allografts demonstrated very high tissue levels in the treated graft (37.5±25.3 ug/g), while the control grafts demonstrated relatively low tissue levels (1.6±0.6 ug/g) at 36 days post-transplantation. These results were obtained with a formulation that produced site-specific efficacy in vivo, using a vehicle system comprising lanoline: mineral oil: olive oil: polysorbate 80 (7:7:7:4) and CsA (2.5% w/v). At this time, placebo grafts were undergoing vigorous rejection. The treated graft contained 2,629% greater CsA than the vehicle treated graft. Animal experiments show that local CsA is efficacious and non-toxic. Systemic application is necessary to modulate the immune response in accord with the known mechanisms of actions of cyclosporine (see FIG. 5). In addition, as wound healing is expedited with systemic administration, a nidus of inflammation is therefore avoided.

The results in tissue culture systems and in vivo demonstrate that prior systemic cyclosporine treatment sensitizes both basal and activated immunocytes to become more responsive to secondary exposure to immunosuppressants for increased efficacy at a local level. In addition, high concentrations must be delivered to the local site to achieve such efficacy. This likely models an activated autoimmune disease state in tissue such as psoriasis in skin.

Figure 1A:
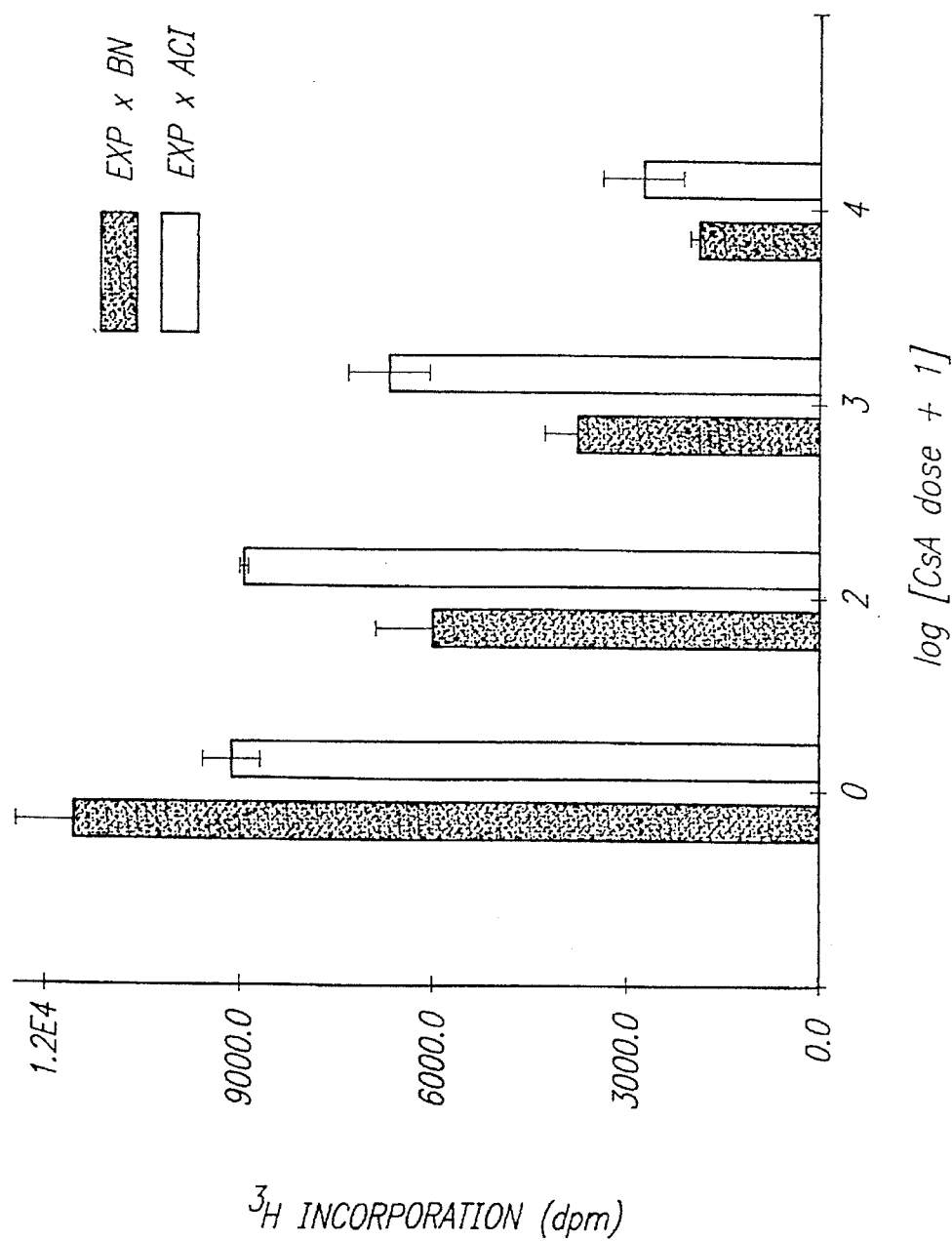
FIGS. 1 A, B and C show in vitro site specific mixed lymphocyte responses of peripheral lymphocytes in the presence of varying concentrations of cyclosporine: A) topical and systemic treatment, B) systemic treatment alone, and C) naive cells.
Figure 1B:
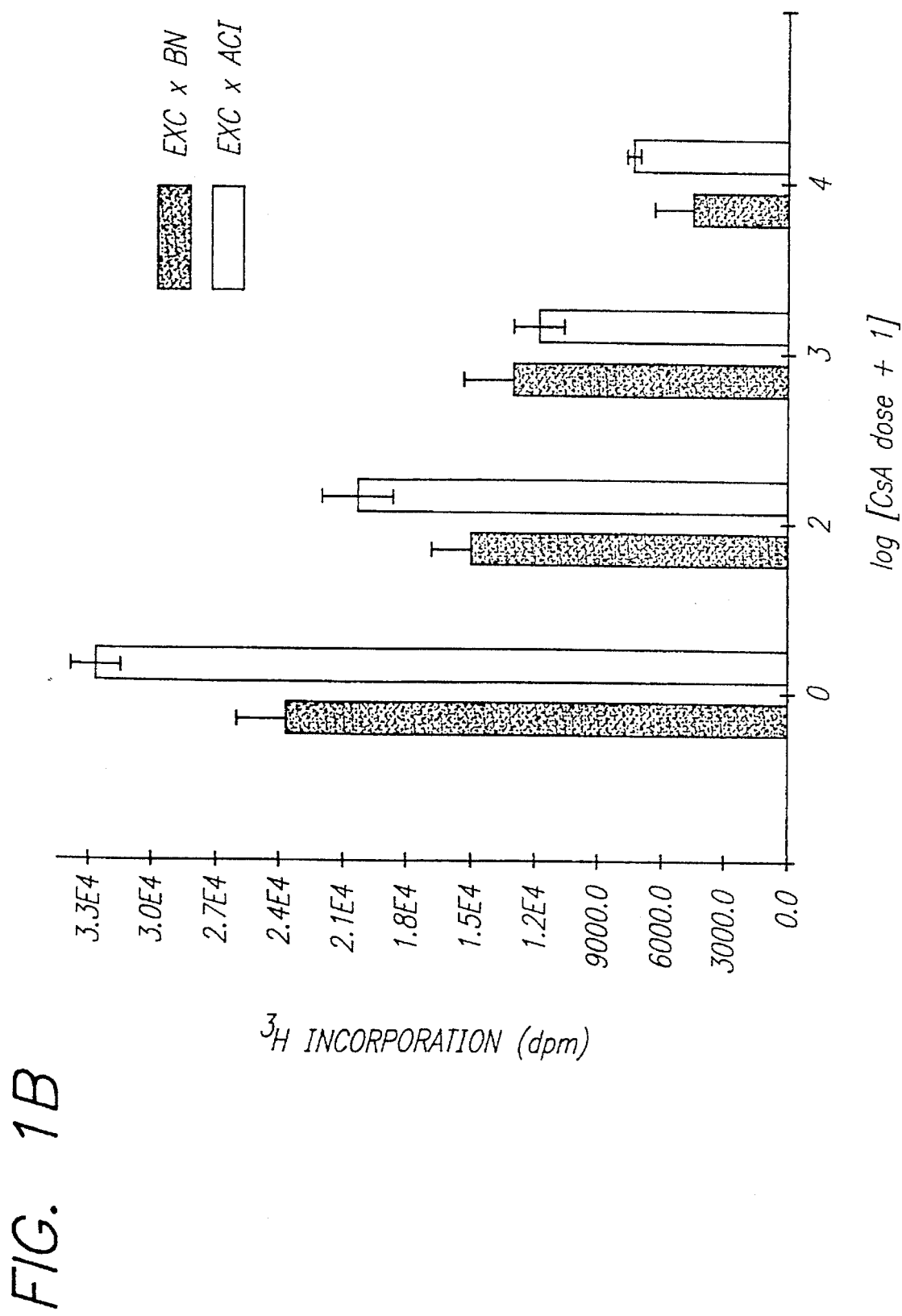
Figure 1C:
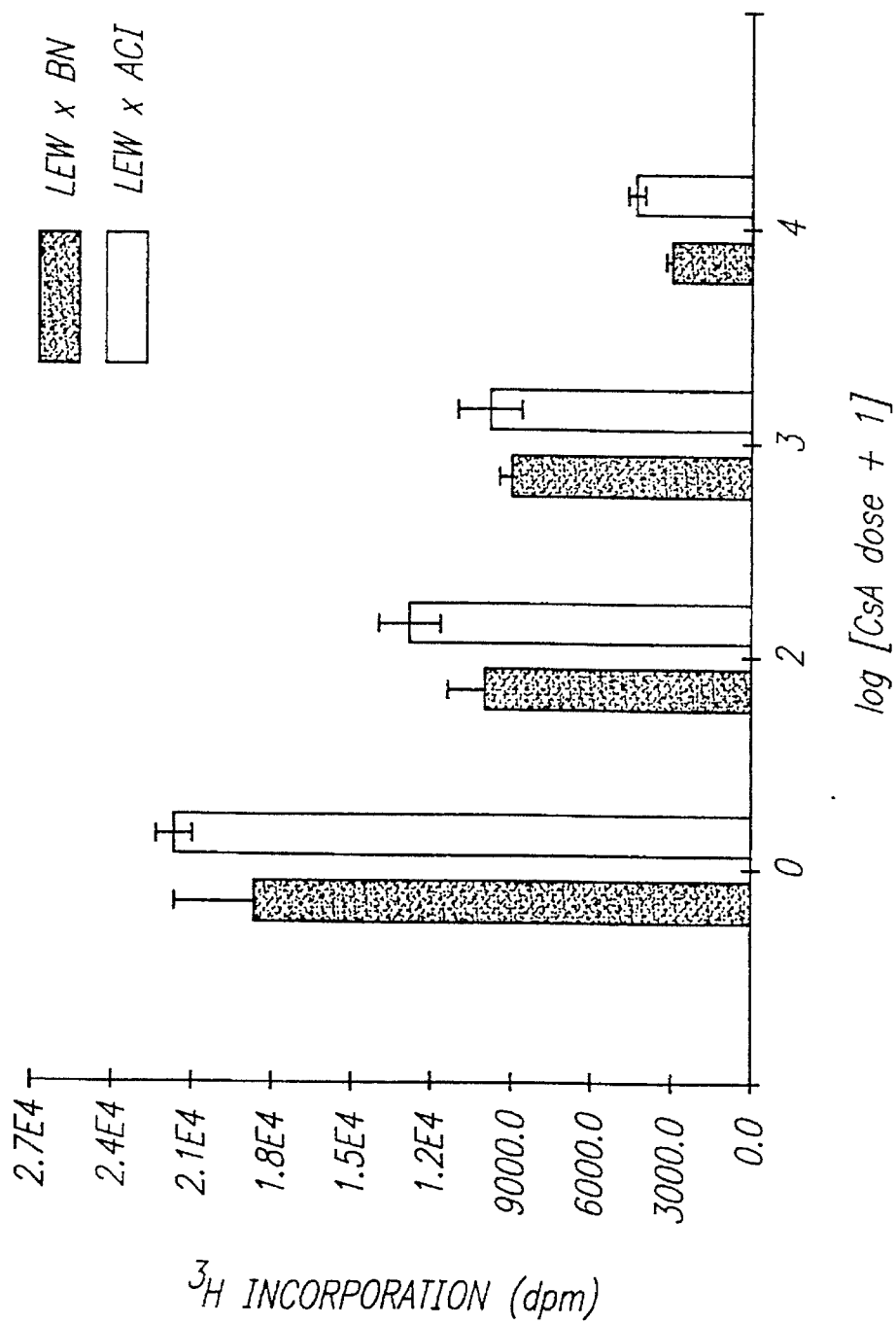

More specifically, data shows that to inhibit an ongoing inflammatory immune response, a key factor is that cyclosporine must be delivered locally at high concentrations (>10,000 ng/gm or ml) during primary topical treatment. Another important item is that prior cyclosporine exposure can greatly influence site-specific effects. Thus, more efficacious immune modulation at a systemic level predisposes to increased efficacy, locally (FIGS. 1 and 4). In addition, immunogenicity at the local site decreases during treatment. For example, immunocytes obtained from animals following systemic/topical treatment, show increased sensitivity to secondary exposure of cyclosporine at a local level. This occurs both at a basal level and following antigen activation. Thus, based upon pharmacokinetic studies, the dose required to inhibit immune responsiveness locally at half maximal effectiveness (Kd) during secondary exposure is greatly reduced compared to primary exposure. Additionally, these immunocytes also demonstrate antigen specific unresponsiveness (tolerance) and therefore the Kd for immunosuppressant cyclosporine treatment during secondary antigen exposure is also greatly reduced. In practical terms, based upon these data, one concludes that during an activated autoimmune response, the efficacy for topical cyclosporine will increase following combined systemic/topical treatment and with subsequent rounds of local treatment alone.

Both in vitro and in vivo data confirms that CsA does indeed have potent immunosuppressive effects on preactivated cells, as concentrations are increased to relatively high values locally (FIGS. 1 and 4). Such levels in the systemic circulation would normally be expected to produce organ toxicity. However, high levels of CsA can be localized at the tissue site undergoing immune activation. Animal experiments show that local CsA is efficacious and non-toxic.

Test Systems

Topical formulations of cyclosporine, rapamycin, and other anti-inflammatory compounds have been successfully developed and tested in animal studies. They have been studied for transdermal penetration and their ability to effect localized anti-inflammatory responses in the skin. Certain principles have been defined, with respect to the vehicle (see below), as important and necessary for efficacy. In addition, dose and timing requirements have been studied and a critical method has been identified for successful treatment. In addition, a novel skin graft animal model has been developed to screen anti-inflammatory formulations, their efficacy, toxicity, and mechanisms of action.

Our hypothesis to achieve local efficacy is to deliver high levels of the immunosuppressive compound at the site of highest immune cellular interactions. Therefore, a depot effect of the active principle in the dermal tissues or high concentration gradient would be the desirable result. In studies with various formulations, none have generated measurable levels of CsA in aqueous transdermal collecting solutions using in vitro diffusion chambers. This data includes formulations that have clearly demonstrated transdermal CsA levels and efficacy in vivo (FIG. 6).

Figure 6A:
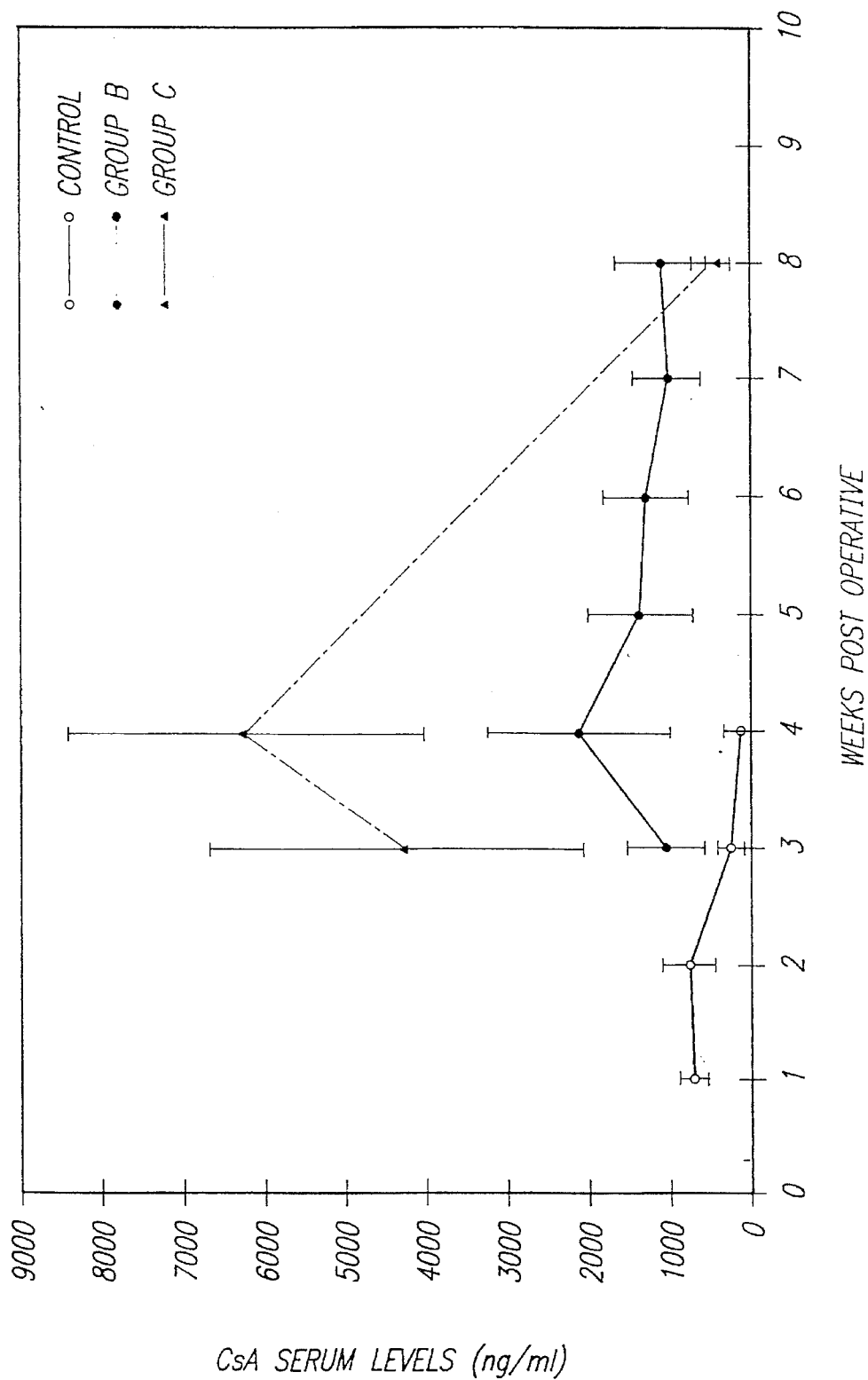
FIGS. 6 A, B and C show transdermal delivery of immunosuppressant with various vehicle systems resulting in systemic serum levels of CsA.
Figure 6B:
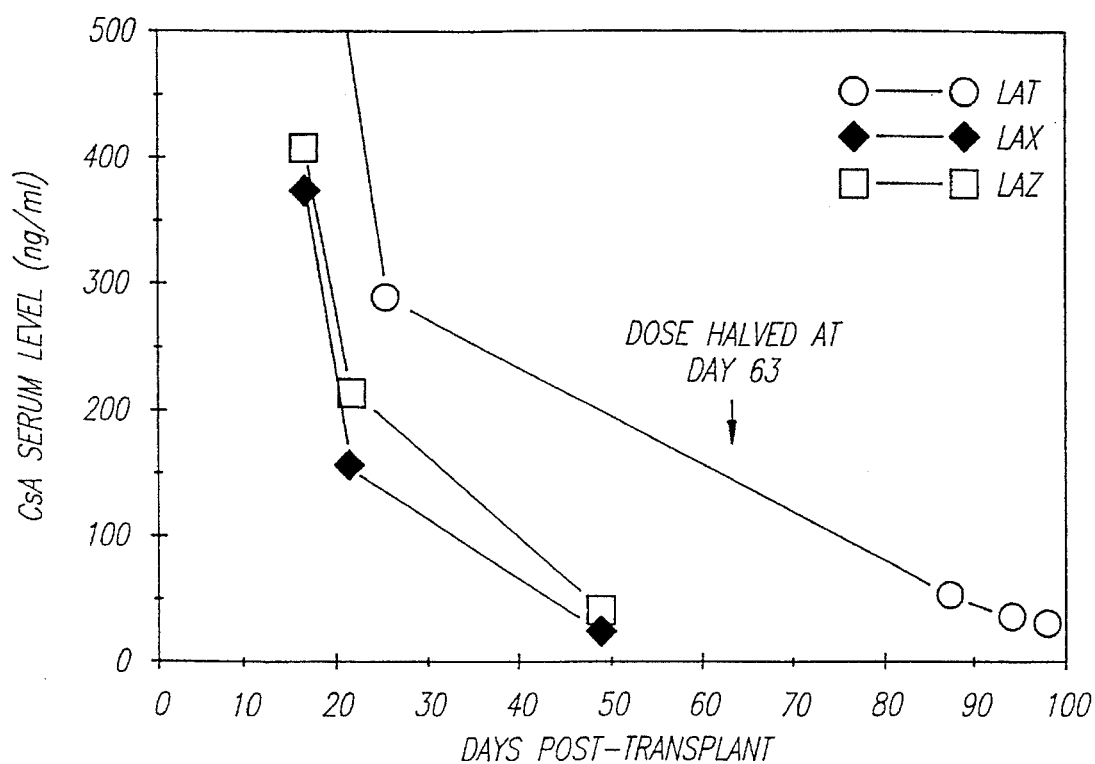
Figure 6C:
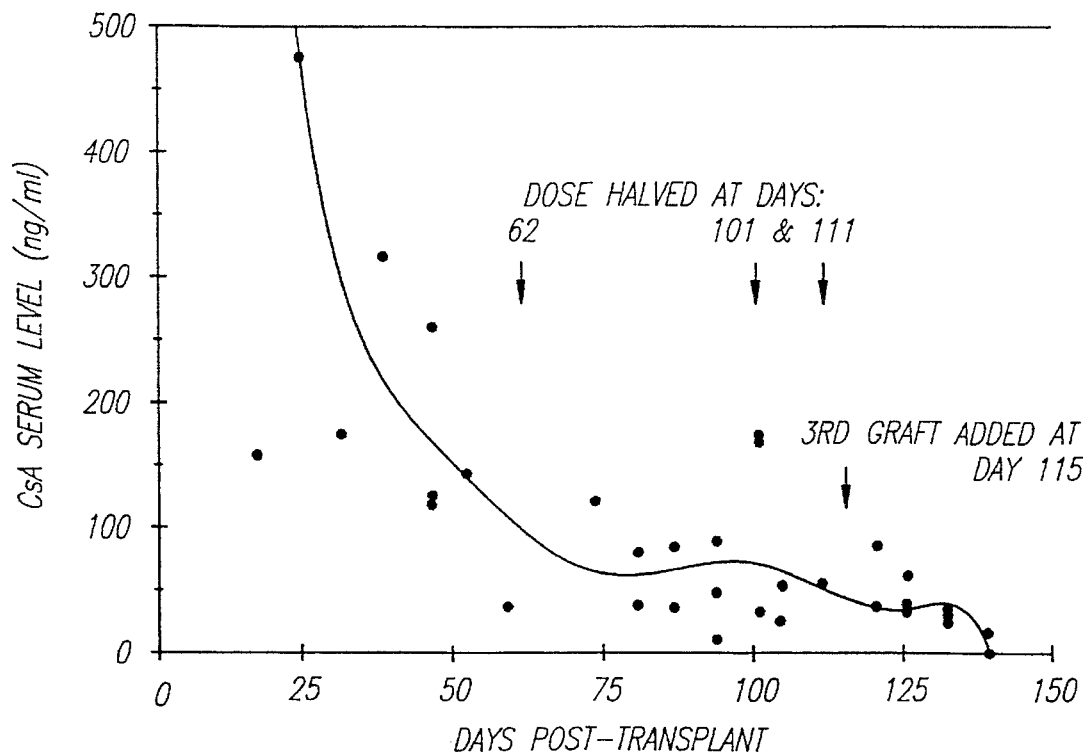
Figure 7:
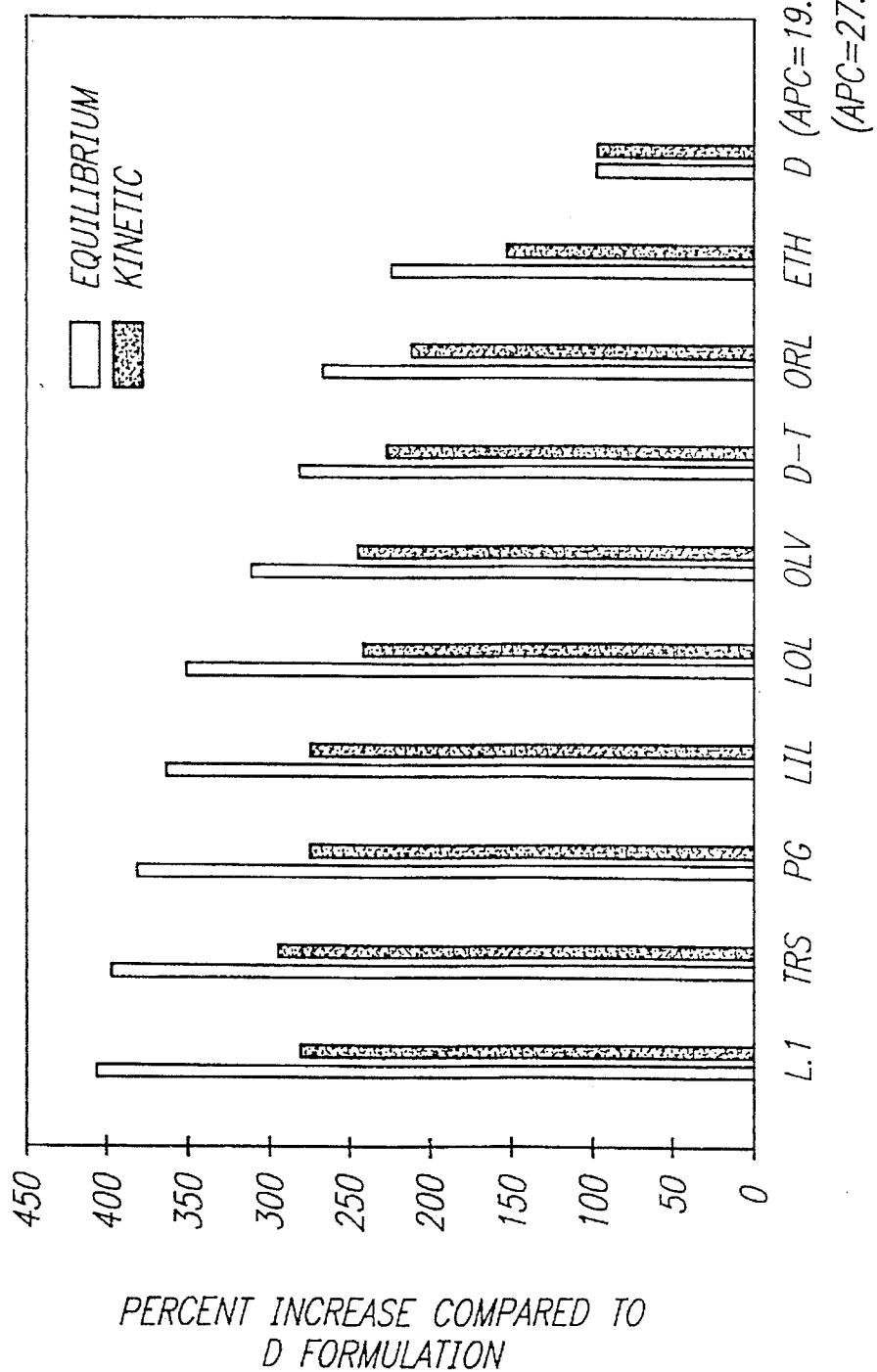
FIG. 7 shows increasing lipophilic delivery of immunosuppressant (CsA) with various vehicle systems.

FIG. 6 shows that certain classes of carriers, can serve as vehicles for transdermal delivery of cyclosporine. Data represented in these examples, demonstrates that some carriers can enable the lipophilic cyclosporines to effect transdermal delivery through the skin and provide systemic therapeutic levels. Vehicle systems that increase cyclosporine's lipophilicity in partition coefficient experiments (high apparent partition coefficients in octanol/HBSS systems) provide increased transdermal delivery in vivo (FIG. 7). An example is ethyl alcohol: propylene glycol: glycerine (1:6:3) and CsA (2.5% w/v; formula L.1). Vehicle systems that decrease cyclosporine's lipophilicity provide depot effects in vivo (FIG. 7). In FIG. 7: L.1 is Ethanol:1,2 Propanediol:Glycerine (1:6:3); TRS is Diethylene glycol monoethyl ether (transcutol); PG is 1,2 Propanediol; LIL is Vegetable oil PEG-6 complex (Labrafil); LOL is Labrasol= Glyceryl caprylate/caprate (and) PEG-8 caprylate/caprate (Labrasol); OLV is Olive oil; D-T is Lanoline: Mineral oil: Olive oil (1:1:1); ORL is Oral Sandimmune Liquid; ETH is EtOH (Ethanol); and D is Lanoline: Mineral oil: Olive oil:Polysorbate 80 (1:1:1:0.57).

With regard to in vitro test systems of skin penetration, due to insolubility of the lipophilic active in standard aqueous based collecting solutions used for in vitro chamber studies, the value of such analyses is questionable. An example of in vitro results from one formulation that is known to act transdermally in vivo is shown in Table I. As can be seen, CsA is clearly deposited in the skin. The distribution is presented as a percent of the total amount of CsA detected in pig skin.

TABLE I

| stratum corneum | 11% |
| epidermis | 75% |
| dermis | 14% |
| chamber solution | 0% (undetectable) |

Therefore, one of the most important factors in topical immunosuppressive therapy is to localize the compound in the area of cellular activity. This increases the efficacy of the compound and decreases the toxicity to uninvolved organ systems. In vitro diffusion chamber tests on certain formulations support the premise that CsA localizes in the skin (stratum corneum, epidermis and dermis) with very little penetrating transdermally into the aqueous chamber solution. In vivo test results have confirmed our hypothesis that such in vitro assay systems are not completely adequate for evaluating topical cyclosporine and other lipophilic immunosuppressants. Conclusions must be derived in conjunction with in vivo test results. In vivo models have been designed that provide superior test systems concerning absorption and functional data in these situations. The functional results of local immunosuppressive therapy are much more relevant to the clinical situation and are detailed below.

In Vivo Penetration Studies

Various topical drug formulations have been successfully devised, incorporating certain chemical properties within the drug vehicle (see below). Certain classes of carriers, or combinations thereof, can serve as vehicles for lipophilic immunosuppressants such as cyclosporine which enable the active principle to penetrate and localize within the skin tissue (see FIGS. 3,8,9). It has been proven that this is one of the key factors in achieving local efficacy at the tissue site without evidence of systemic delivery or actions. However, other carriers can enable lipophilic immunosuppressants such as cyclosporine to effect primarily transdermal delivery through the skin and provide systemic therapeutic actions (FIGS. 6A, B and C).

Site-specific immune suppressive drugs can be formulation dependent

Some formulations are not efficacious. This is congruent with published results from other investigators. Surprisingly, however, certain formulations have been found extremely efficacious. Certain principles have been defined as necessary to achieve site-specific immunosuppression by topical cyclosporine. These principles are detailed below.

Certain classes of carriers, can serve as vehicles for transdermal delivery of cyclosporine. Data represented in these examples, shows that some carriers can enable the lipophilic cyclosporines to effect transdermal delivery through the skin and provide systemic therapeutic levels. Vehicle systems that increase cyclosporine's lipophilicity in partition coefficient experiments (high apparent partition coefficients in octanol/HBSS systems) provide increased transdermal delivery in vivo (FIGS. 6–8). Vehicle systems that decrease cyclosporine's lipophilicity provide depot effects in vivo (FIGS. 6–8).

Results were derived from determination of partition coefficients into lipophilic/hydrophilic phases with different immunosuppressant vehicle solvent systems as follows. One-Octanol was chosen as the hydrophobic phase because it is widely believed to mimic biological lipophilic environments. RPMI was used as the aqueous phase in order to mimic extra cellular fluid. All vehicles were prepared by a standard protocol at 60° C. Vehicles were spiked with radio-labelled tritiated drug solution (Sandoz).

Fifty ml of 1-octanol and fifty ml of RPMI were added to a fleaker with constant stirring. The mixture was then vigorously mixed for two hours at 4° C. The solution was then removed from the refrigerator and placed in a fume hood and allowed to separate for two hours. The 1-octanol layer was then removed. To five ml of the 1-octanol saturated RPMI, 500 μl of tritiated vehicle at 60° C. was added with vortexing. The same procedure was also completed with non-labeled vehicle. The tubes were then placed in a tube rotator at 17 RPM for 48 hours at room temperature, 24° C. The samples were then centrifuged for 10 minutes at 1155×g. Three 1 ml samples of the octanol layer of each tube was removed and put in a separate 13 ml scintillation vial. About 3 ml of the interface was then removed and three one ml samples of the RPMI layer drawn from the bottom of the tube were then placed in three separate scintillation vials. Thirteen ml of ecoscint were then added to each of the scintillation vials and their counts were measured using a liquid scintillation counter.

Functional/Pharmacology Data

Figure 8C:
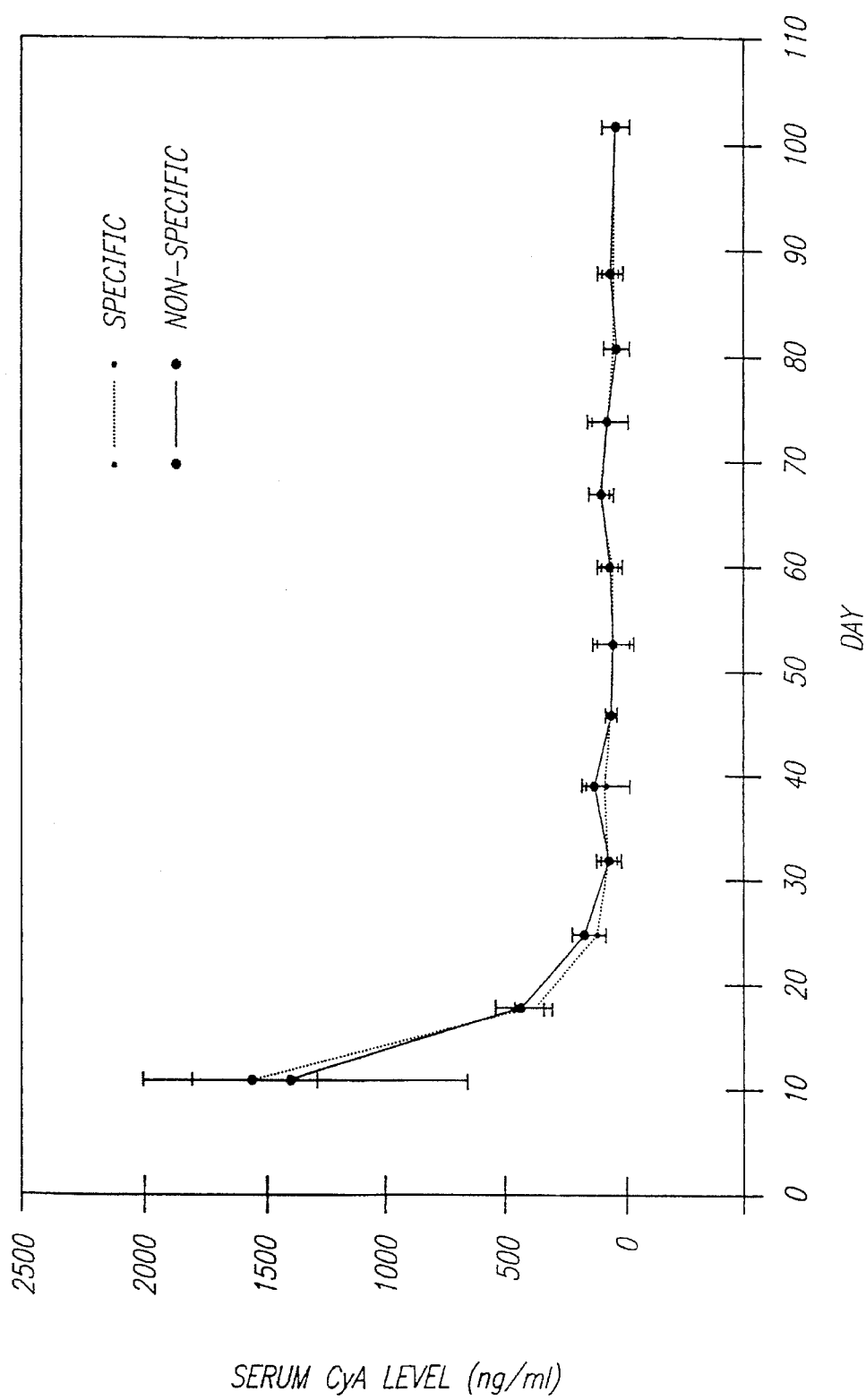
FIGS. 8 A, B and C show site-specific (depot) delivery of CsA without transdermal effects and absence of systemic serum concentrations.
Figure 9:
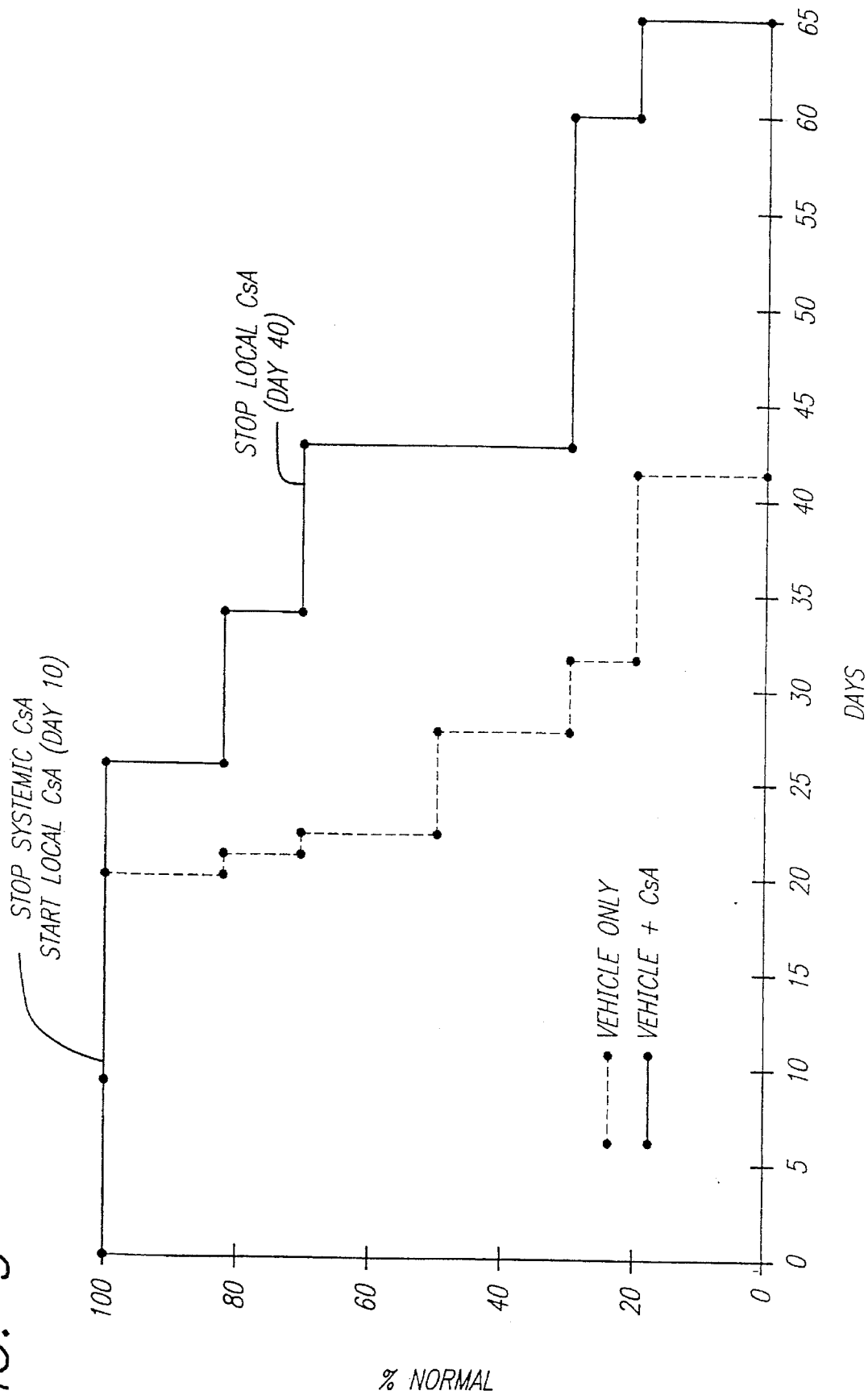
FIG. 9 shows localized site-specific immunosuppressive effects of topical immunosuppressant (CsA) in vivo using a dual skin allograft model.
Figure 10A:
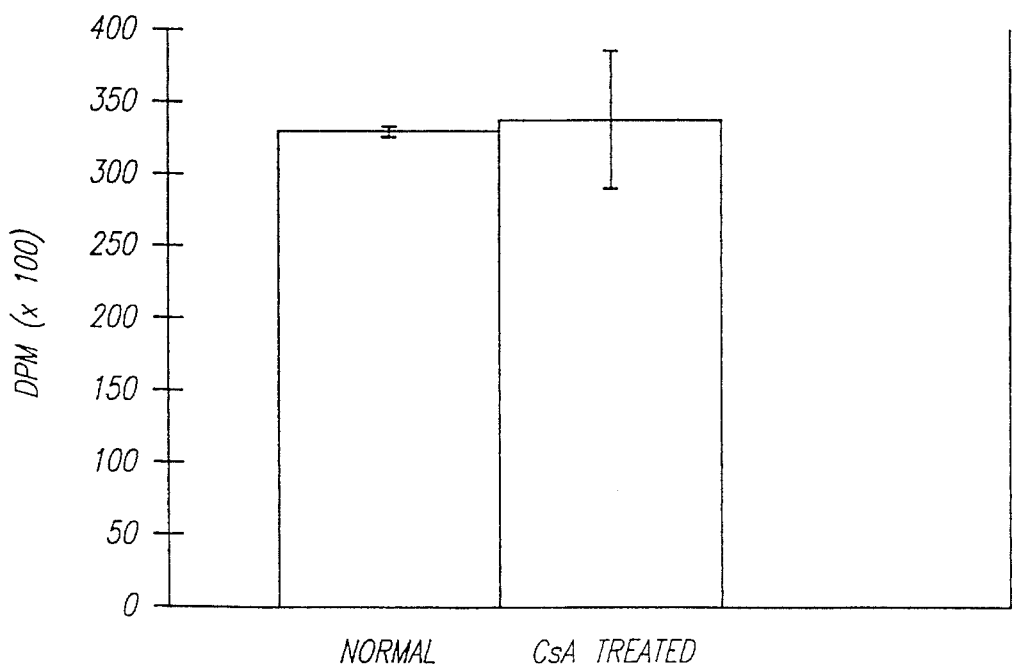
FIGS. 10 A and B show mitogen stimulation responses of systemic peripheral lymphocytes during site-specific immunosuppression with topical cyclosporine: A) CON A, and B) PHA.
Figure 10B:
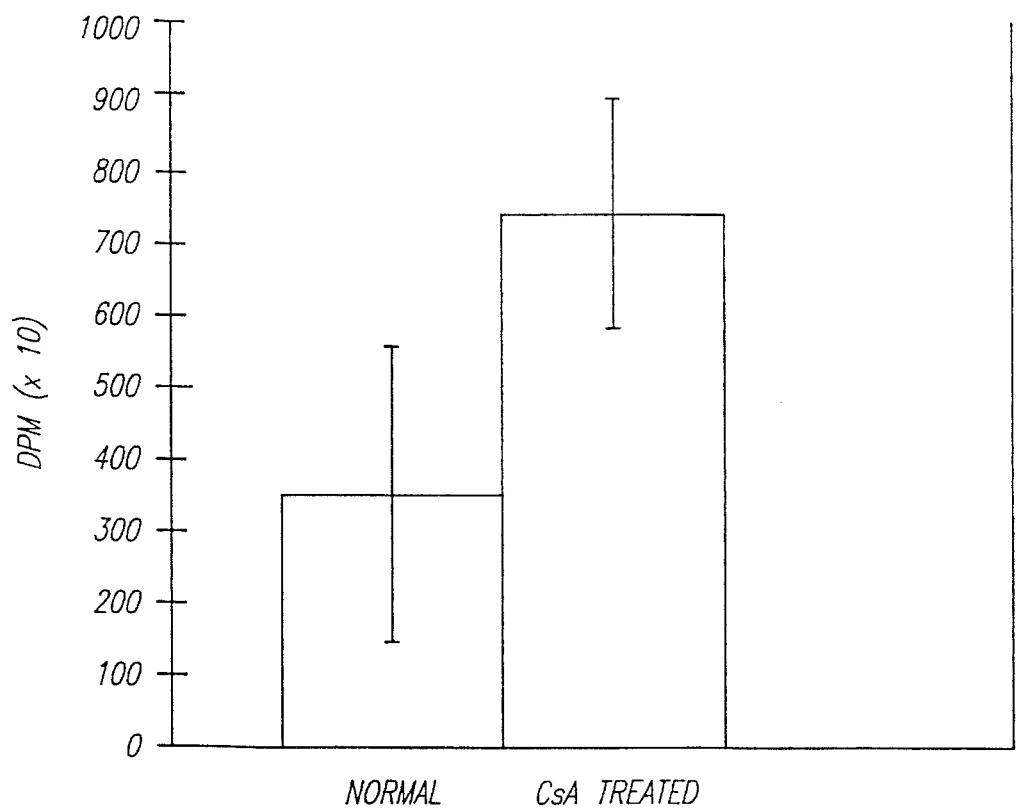

These studies show that one can partition CsA into the skin and inhibit functional immune responses (T cell activation and inflammatory reactions) at a local level without significant influence on systemic immunity (FIGS. 9 and 10). Anti-inflammatory efficacy was proven both grossly, histopathologically, and immunologically in the presence of locally administered CsA. CsA levels were low systemically, and showed relative site-specificity in terms of tissue concentration. Interestingly, of the CsA that can be measured in the serum and is derived from transdermal delivery, it appears to be parent compound (FIG. 8C). An antibody was utilized to determine serum CsA concentration which was directed against parent compound for the specific assay and another that was directed against metabolites for the non-specific assay. The data suggested that very little metabolism of the parent compound takes place during transdermal delivery.

Functional Immune Data

Figure 11:
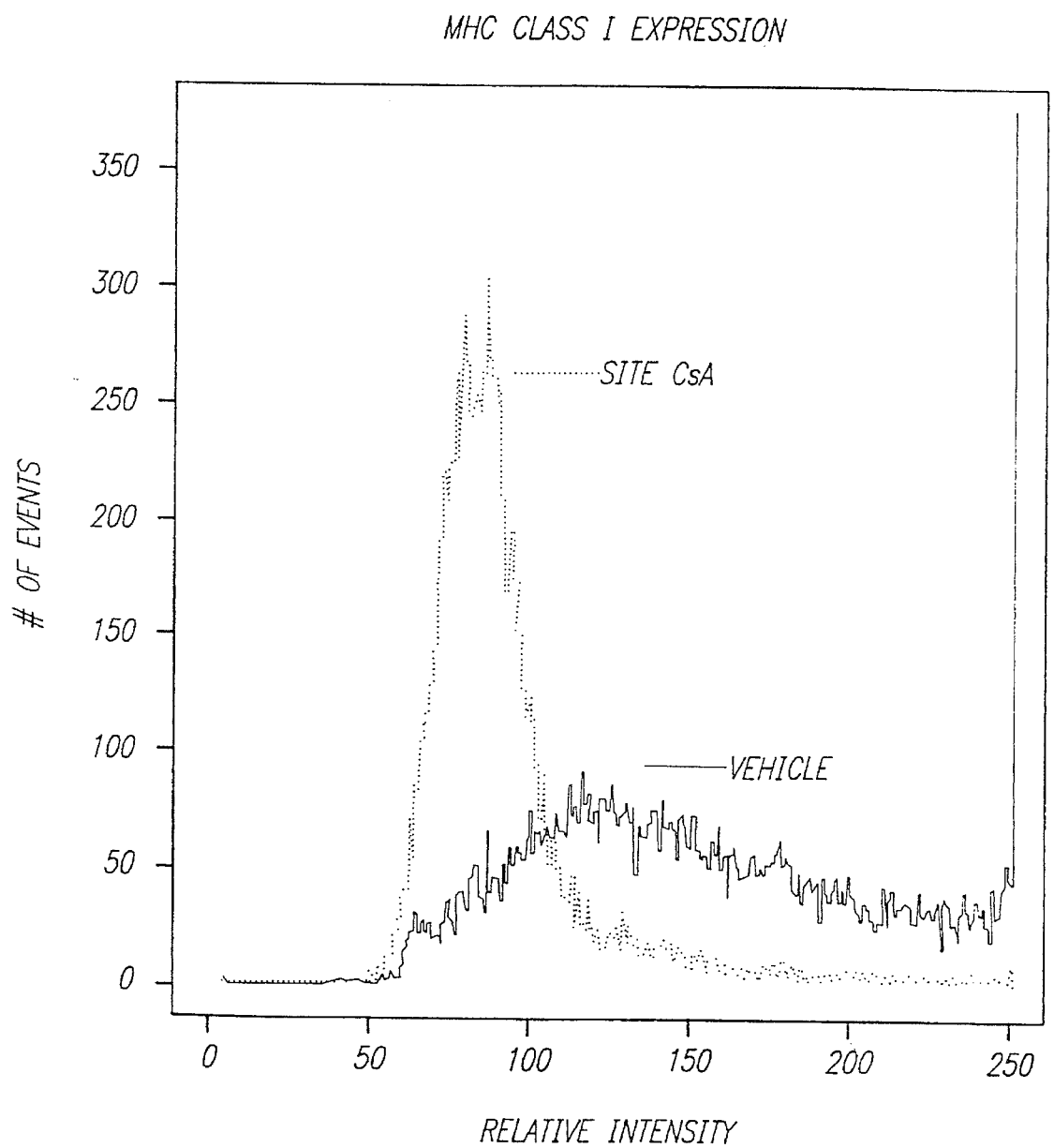
FIG. 11 shows decreased expression of major histocompatibility complex I determinants in topical CsA treated skin grafts compared to rejecting vehicle treated grafts.
Figure 12A:
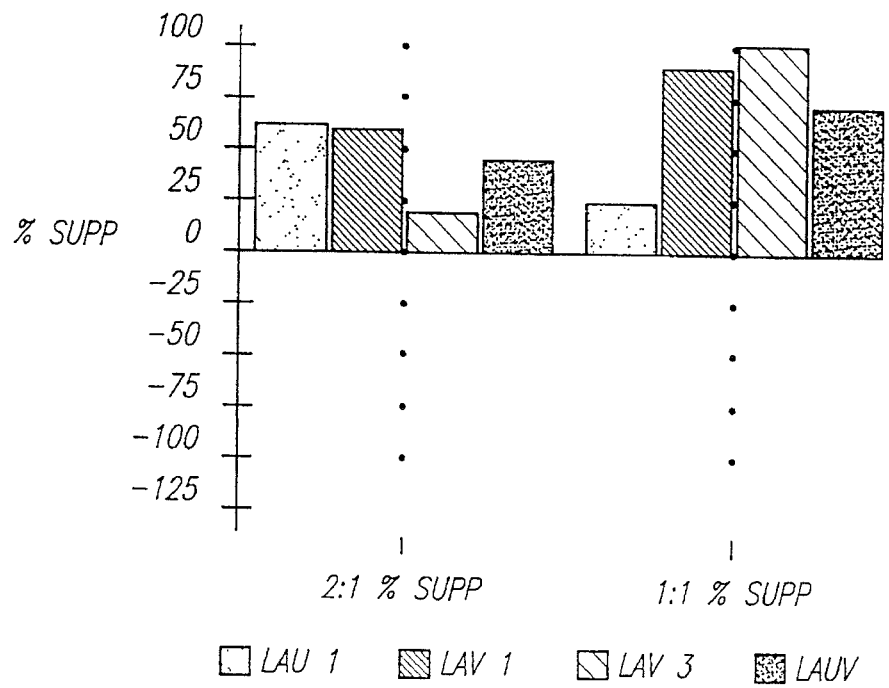
FIGS. 12 A and B show antigen-specific suppressor cell assays of systemic peripheral lymphocytes during site-specific immunosuppression with topical cyclosporine: A) antigen specific T-suppressor cell response; and B) non-specific suppressor T-cell response.
Figure 12B:
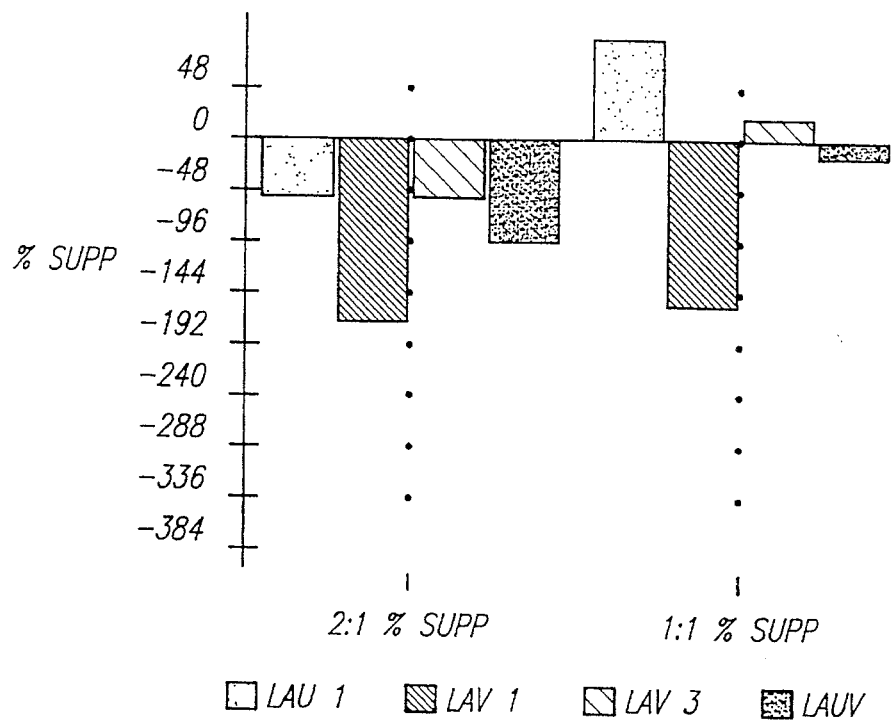

A number of experiments have been devoted to understanding immune mechanisms involved in topical cyclosporine's action. In summary, it has been shown that localized cyclosporine down regulates the expression of both MHC class I and II target antigens compared to placebo treated grafts as determined by immunohistochemistry (FIG. 11). This may inhibit antigen presentation by APCs, T cell recognition, binding, cellular communication, and maturation. Moreover, topical cyclosporine has been shown to inhibit either the infiltration or proliferation of CD4+ MHC class II responsive T helper cells locally. In addition, data supports the hypothesis that systemic antigen specific suppressor cells and/or clonal deletion develops following antigen stimulation and local CsA treatment (FIG. 12). This latter finding is very important because it demonstrates that efficacious immune modulation at the site of activation can have profound beneficial influence upon systemic immunity, with reduced side effects.

Figure 13B:
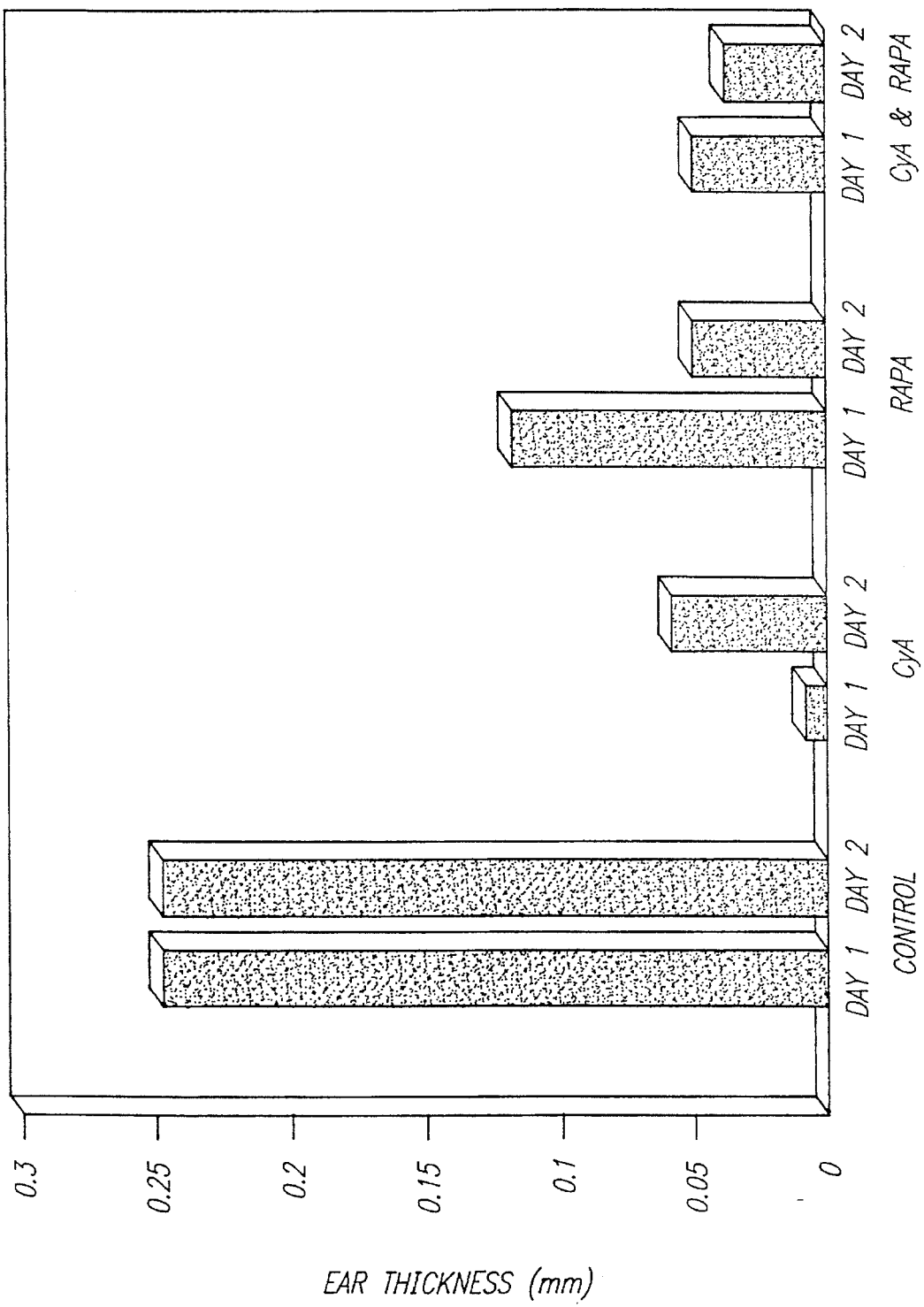
FIGS. 13 A and B show the effect of multiple agents in combination with cyclosporine on topical immunosuppression: A) steroid combined with CsA in a dual skin graft model; and B) rapamycin alone and in combination with CsA in a skin contact dermatitis model.
Figure 14A:
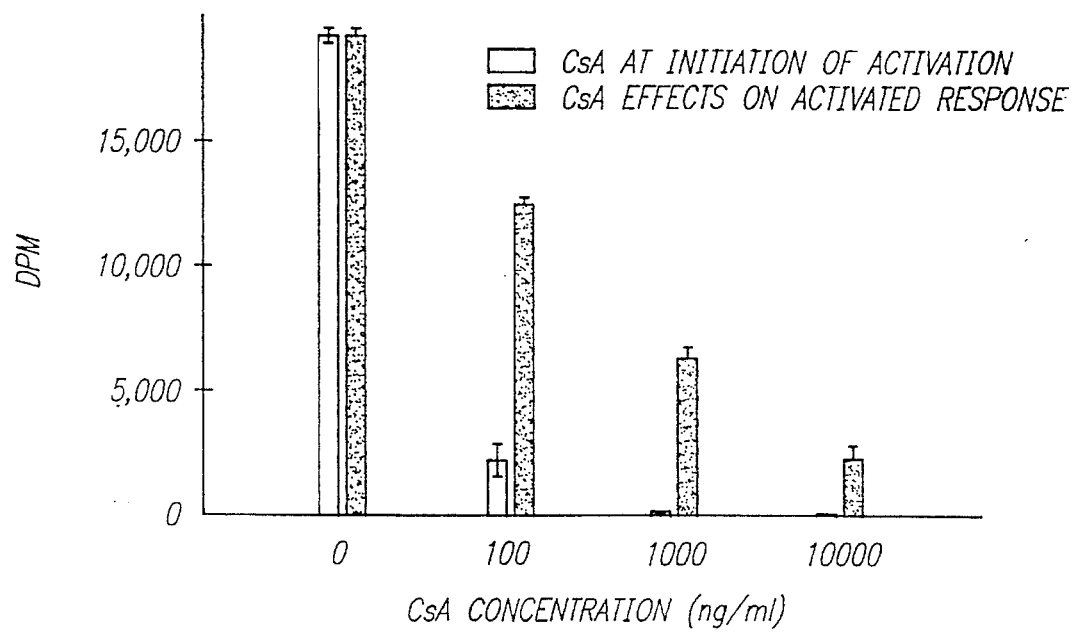
FIGS. 14 A and B show site-specific immune suppression of either primary or activated in vitro models of cellular immune responses by varying concentrations of: A) cyclosporine, or B) rapamycin.
Figure 14B:
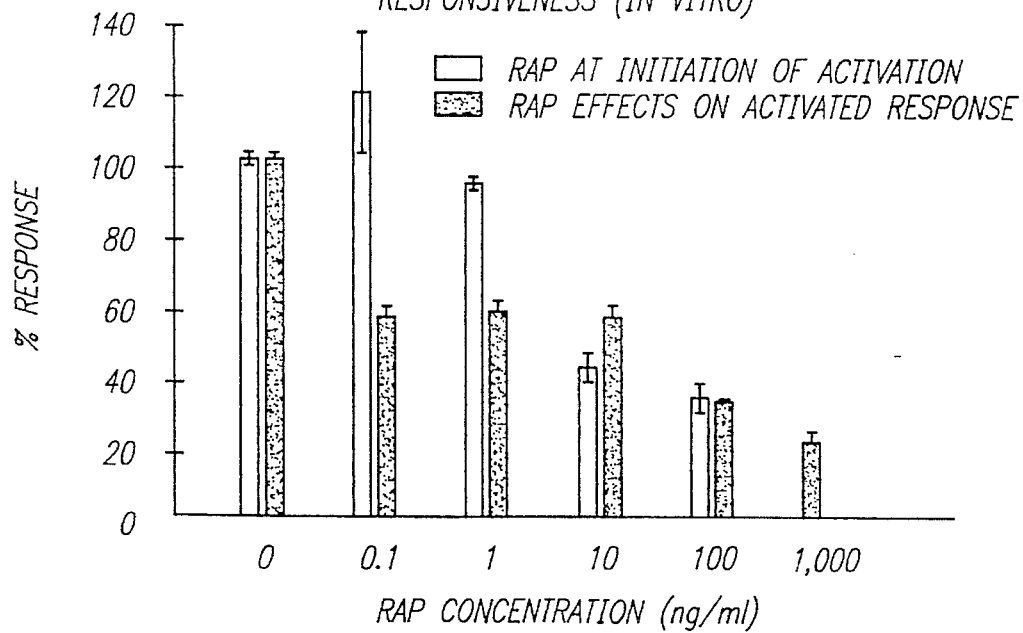

Topical drug formulations which combine active agents to synergistically attack multiple disease mechanisms at a local site-specific level Results above demonstrate that multiple classes of active agents can be successfully combined to produce new and extremely potent topical drugs (see FIGS. 2 and 13). The liquid pharmaceutical composition used in FIG. 13A comprised a novel immunosuppressive drug, a steroid or corticosteroid, and a carrier consisting of the following: (1) an esterification product of natural triglycerides and polyethylene glycol which may be prepared according to U.S. Pat. No. 3,288,824; (2) a vegetable oil; and (3) ethanol.

The preferred immunosuppressant is cyclosporine A and the preferred corticosteroid is hydrocortisone. The preferred embodiment contains CsA to corticosteroid 2.5 to 1 (i.e., range CsA 0.1% to 25%: corticosteroid 0.01% to 10%; preferred range 2.5% CsA: 1.0% hydrocortisone). The preferred embodiment contains ester to cyclosporine in a weight ratio of about 10:0.2 to 10 parts by weight; vegetable oil is 35 to 60% of the total composition by weight; and ethanol is 1 to 20% of the total composition by weight. The steroid is not limited to hydrocortisone.

For example, a topical oleaginous ointment base comprising the combined active ingredients of cyclosporine and an off-patent steroid, hydrocortisone, provide significant increased efficacy. In this instance, a relatively weak corticosteroid (hydrocortisone) was successfully combined with CsA to provide extensive and site-specific graft prolongation with topical treatment. However, induction of immune unresponsiveness in this situation is critically dependent upon a local phase of cyclosporine treatment independent of other immunomodulators. Thus, new compounds that combine more than one active principle with cyclosporine can be designed to synergistically attack multiple inflammatory mechanisms and functions with reduced side-effects. This affords the opportunity for developing novel local immunosuppressants based topical drugs by combining off-patent active principles and/or other promising new agents.

Examples of other agents that could analogously be combined with novel microorganism derived immunosuppressants in a single topical formulation in order to potentially enhance efficacy include but are not limited to: Betamethasone dipropionate; betamethasone valerate; fluocinolone acetonide; triamcinolone acetonide; prednisone; methylprednisolone; prednisolone indomethacin; sulindac; ibuprofen; aspirin; naproxen; tolmetin; azathioprine; cyclophosphamide; deoxyspergualin; bredinin; didemnin B; methotrexate; and thalidomide. Other additional actives and potential combinations are listed below.

cyclosporine-rapamycin synergism

As discussed above, immune/inflammatory reactions can be inhibited via topical use of cyclosporines, alone and in combination with other anti-inflammatory agents, and more particularly, with Cyclosporine A alone or combined with steroidal anti-inflammatory agents such as hydrocortisone to produce synergistic results. However, multiple immunosuppressant agents can be combined, particularly with CsA, to produce potent topical immunosuppressants. In the instance described above, a relatively weak corticosteroid (hydrocortisone) was successfully combined with CsA to provide extensive and site-specific graft prolongation. (FIGS. 2, 13A).

Topical Rapamycin (Alone without combination)—examples of site-specific in vitro models Rapamycin or CsA alone, provided potent site-specific immune suppression in either primary or activated cellular immune responses as in vitro models of local immune suppression. Cyclosporine or rapamycin inhibited primary inflammatory/immune responses by local application in mixed lymphocyte responses (FIGS. 14 A and B). Rapamycin was surprisingly efficacious with local application during both late and early inflammatory immune phases. Cyclosporine was particularly efficacious locally during the early inflammatory immune phase compared to the late phase (FIGS. 14 A and B).

Examples of site-specific in vivo models alone, and in combination

Consistent with these in vitro findings, either cyclosporine or rapamycin inhibited local inflammatory/immune responses by topical application to skin tissue undergoing hypersensitivity responses. This included site-specific immune suppression effected by topical use of cyclosporine and rapamycin combinations in contact hypersensitivity reactions of skin tissue (FIG. 13B). In FIG. 13B, rapamycin, alone, and in combination with CsA, provided new potent site-specific topical drugs in a mouse contact dermatitis model. Rapamycin (0.01%), cyclosporine (0.1%), and rapamycin-cyclosporine (0.01%/0.1%) combined formulations, were applied in a trinary drug delivery system consisting of 1,2 propanediol, diethylene glycol monoethyl ether, and a glyceryl caprylate/caprate polyethylene glycol complex. This vehicle system was surprisingly effective at inducing site-specific immune suppression even at these low concentrations of novel immune suppressants. Additionally, as discussed previously, a relatively weak corticosteroid (hydrocortisone) was successfully combined. Therefore, multiple agents can be combined with CsA to produce potent topical immunosuppressant drugs.

Similar to the in vitro data, rapamycin was particularly efficacious during the late local inflammatory-immune phase in this latter example, and cyclosporine was particularly efficacious during the early local inflammatory immune phase. Rapamycin (alone), at concentrations as low as 0.001%, provided surprising site-specific immune suppression. In addition, cyclosporine (0.01%) alone, was surprisingly efficacious using the particular delivery system detailed above. Rapamycin in combination with CsA (0.001%/0.01%), also provided unexpected site-specific immune suppression by topical application in this mouse contact dermatitis model using the same delivery system.

To further elaborate, rapamycin (0.001%), cyclosporine (0.01%), and rapamycin-cyclosporine (0.001%/0.01%) combined formulations, were applied in a trinary drug delivery system consisting of 1,2 propanediol, diethylene glycol monoethyl ether, and a glyceryl caprylate/caprate polyethylene glycol complex (6:3:1). Rapamycin derivatives and analogs, and other immunophilin binding macrolides and immunosuppressive agents shall similarly be effective using these methods and delivery systems.

Other anti-inflammatory immunosuppressant combinations that can similarly be used include but are not limited to the following: DSG and analogs; mycophenolic acid derivatives—RS 61443; purine and pyramidine blockers; brequinar and derivatives; immunophilin binding immunosuppressants; macrolide immunosuppressants; FK506 and derivatives; and others.

Other immunosuppressants (alone) for site-specific effects can include but are not limited to the following: DSG and analogs; mycophenolic acid derivatives—RS61443; purine and pyramidine blockers; brequinar and derivatives; immunophilin binding immunosuppressants; macrolide immunosuppressants; FK506 and derivatives; and others.

Other site-specific applications and compositions can include but are not limited to the following: pumps; shields; liposome formulations; microemulsion formulations; encapsulations; lipid emulsions; organ perfusion; ophthalmic, shampoo, mouthwashes, ear, inhalants, suppositories, joints etc.; systemic/site-specific combinations; patch, solid and transdermal delivery systems; and formulations for site-specific injection as in joints for inflammatory/immune conditions including rheumatoid arthritis.

Localized site-specific efficacy within skin tissue

Non-polar oleaginous hydrophobic/lipophilic carriers, or combinations thereof, can serve as vehicles for novel lipophilic immunosuppressants, such as the cyclosporines. In these instances, certain oleaginous carriers enable the lipophilic active principle to penetrate the epidermal barrier, depot within the tissue in high concentrations, and effect local site-specific immunosuppression. It has been proven that such classes of carriers are one of the key factors in achieving local efficacy at the tissue site without evidence of systemic delivery or actions. Examples of such hydrophobic carriers which have been tested and shown to uphold these principles include but are not limited to the following or combinations thereof: Anhydrous Lanolin; Petrolatum; Vegetable Oils; Mineral Oils; Jojoba Oil; and other oils and waxes.

Transdermal drug delivery through skin tissue

Most surprisingly and in contradistinction to the results above, broadly efficient polar organic solvents, carriers, or combinations thereof, can enable novel lipophilic immunosuppressants derived from microorganisms, using cyclosporine as a model, to effect transdermal delivery through the skin. These solvent systems are effective solubilizers of immunosuppressants. In general, solubilizing efficiency of the solvent systems, the solubility of the active compound, and the polar nature of the organic carriers appears to influence levels of transdermal drug delivery. These solvents can be combined to make efficient solvent systems, preferably, consisting of binary and trinary systems.

For example, solvents and carriers demonstrating solubility in, or miscibility with a broad range of organic solvents, and even water are preferred. Ethoxylates such as diethylene glycol monoethyl ether is a preferred lipo- and hydrosoluble solvent. It is miscible with acetone, benzene, chloroform, ethanol, and water. Another preferred class of solvents are hydrosoluble oils with moderate to high HLB valves. Another preferred class of solvent is glycolysed ethoxylated C8/C10 glycerides such as glyceryl caprylate/caprate and polyethylene glycol caprylate/caprate, also known as Labrasol. This solvent is a hydrosoluble oil with a high HLB value of 14 and soluble in ethanol, chloroform, and water. Another preferred solvent is propylene glycol which is miscible with water, acetone, chloroform, and essential oils. Glycolysed ethoxylated glycerides with moderate to high HLB values are also preferred co-solvents and carriers including amphipathic esters such as vegetable oil polyethylene glycol-6 (PEG) complexes (Labrafils), and similar agents.

Other preferred solvents and carriers satisfying the physico-chemical criteria above include but are not limited to: diethylene glycol diethyl ether, dimethylformamide, dimethyl sulfoxide, ethylene glycol monoethyl ether, polysorbates, polyethylene glycol, polyoxyethylene esters and alcohols. Preferred solvent and co-solvent combinations for transepidermal and transdermal delivery are trinary and binary systems. One preferred composition is a trinary drug delivery system consisting of 1,2 propanediol, diethylene glycol monoethyl ether (Transcutol), and a glyceryl caprylate/caprate polyethylene glycol complex (Labrasol). Ratios of the individual excipient components within this system may vary, but, are preferably 6:3:1, respectively. The solvent system can include a single component or multiple components and range from 20%–100% but preferably is greater than 50% of the total composition.

Transdermal delivery of cyclosporine in these systems results in systemic levels of parent compound, almost exclusively compared to derivatives. In these instances, such carriers will localize cyclosporine within the tissue in high concentrations, creating a gradient to the systemic circulation. If delivered locally at high concentrations, systemic effects can result. However, at lower immunosuppressant concentration gradients, using this class of solvents, site-specific efficacy can be achieved without systemic effects. It has been proven that such classes of carriers are one of the key factors in achieving transdermal drug delivery and systemic actions. However, unexpectedly, it was found that increasing the viscosity of such formulations by thickening agents could retard systemic delivery and effects, and even reduce local site-specific efficacy.

Additional examples of moderately polar solvents, co-solvents and transdermal carriers include but are not limited to the following or combinations thereof: emulsifying bases and solvents with an amphipathic character and moderate hydrophilic to lipophilic balance (HLB) values (≧3.0) including oil-PEG-6 complexes, polyoxyethylene alcohols, and polyoxyethylene fatty acid esters.

DETAILED DESCRIPTION OF THE INVENTION

The present invention provides a method and compositions for abrogating skin allograft rejection, hypersensitivity reactions, and inflammatory reactions. The use of cyclosporine, rapamycin, or combinations of immunosuppressant and other anti-inflammatory agents prolongs the survival of experimental skin allografts, and/or inhibits contact hypersensitivity inflammatory/immune reactions by delivering the drug to the target tissue and increasing efficacy. Systemic therapy alone can be excessively nephrotoxic, hepatotoxic and neurotoxic, and a concomitant increase in infections may pose a significant problem. Use of the present invention, however, circumvents these difficulties and provides a treatment methodology which effectively emphasizes the positive attributes of cyclosporine, rapamycin, and other immunosuppressants while minimizing the detrimental side effects.

EXAMPLES

Topical applications and compositions—steroid synergism

A dual skin allograft model was developed to evaluate mechanisms of site specific immunosuppression with topical immunosuppressants. It was hypothesized that synergistic efficacy could be induced by site specific immunomodulation via antigen-specific mechanisms with topical cyclosporine (CsA) in combination with topical corticosteroids (CS) acting on antigen-independent, nonspecific anti-inflammatory mechanisms. The experiment was designed with a vehicle system that provided less-than-optimal transepidermal delivery and graft prolongation in order to test for potential synergism. Three different protocols were evaluated: 1) Topical CsA (2.5%) at the induction phase through the entire rejection process; 2) Combined topical CsA/hydrocortisone (HC; 2.5%/1.0%) at the induction phase through the entire rejection process; and 3) Topical CsA during the immune induction phase and subsequent addition of combined CsA/HC at initiation of the maintenance phase to full rejection. Topical CsA provided moderate graft prolongation and disparity (FIG. 2). Mean survival times increased slightly with combined topical CsA/HC in comparison to CsA alone, but, did not provide a significant synergism (FIG. 2). However, topical CsA during immune response induction or the antigen-dependent phase with subsequent suppression of antigen-independent inflammation by topical CsA/HC provided dramatic synergism with optimal efficacy and disparity (FIG. 2). Therefore, it was concluded that a local and beneficial immuno-regulatory mechanism was induced by topical CsA during the early immune induction phase which was sensitive to corticosteroids and inhibited during concomitant corticosteroid therapy. However, addition of a corticosteroid during the maintenance phase was necessary for this beneficial mechanism to be expressed.

Cyclosporine and corticosteroids (CS) are widely used immunosuppressive drugs in transplantation and autoimmunity (1–6). However, controversy exists with respect to achieving effective combinational therapy with these drugs for modulating an active on-going immune response.

There exists experimental evidence that both the induction of the immune response and the effector mechanisms during cellular responses are regulated locally at the site of antigenic challenge (1,2,7). In fact, a dual skin allograft model developed in our laboratory provided evidence that site-specific immunosuppression with CsA could modulate immune responsiveness locally (1,2). Our studies established an ongoing Ag-specific driven immune response which is CsA sensitive. Depending on the formulation and CsA concentration delivered locally, this phase can be followed by effector cell generation. Eventually, this effector cell generation may penetrate and escape the CsA coverage leading to the recruitment of non-specific inflammatory components in an environment rich with various mediators. These later phase Ag-independent, lymphokine driven events tend to be less sensitive to the suppressive effects of CsA (1,2,8,9), since CsA is primarily known to work by affecting lymphocyte activation and lymphokine release (9,10). Thus, a localized site-specific modulation of antigen-dependent immune response induction can be hypothesized to be optimally achieved early on. It is also very conceivable that CsA may play an active role at inducing or facilitating the development of local immuno-regulatory mechanisms as well. It has been documented that CsA spares suppressor networks and facilitates regulatory events systemically (10).

Localized corticosteroids would theoretically make a good adjunct as a combinational therapy with topical CsA since they act as potent anti-inflammatory agents and non selective immunosuppressants (11,12) that may inhibit antigen-independent inflammatory reactions. Corticosteroids are believed to work by stabilization of cellular membranes, inhibition of cellular maturation, proliferation, and migration (4,11–14).

We hypothesize that CsA induces and/or facilitates site-specific immunosuppressive mechanisms which could then act synergistically with corticosteroid Ag-independent inflammatory suppression. However, the non-specific immunosuppressive nature of corticosteroids may potentially abrogate putative localized site-specific regulatory mechanisms established under CsA therapy. Therefore, a corticosteroid addition may be detrimental during certain cellular phasic events occurring along the course of immunomodulation. Thus, a timing factor in the addition of a corticosteroid may be crucial in the hypothesized synergistic effect of both immunosuppressive drugs. Indeed, activated inflammatory immune responses have a higher signal sensitivity, different pattern of re-circulation, lower T cell dependence, and a lower antigen concentration requirement (15–20). As stated previously, CsA may be less effective in overcoming a preactivated response (1,2,8), but inclusion of a non-specific, membrane-stabilizing agent like a corticosteroid may provide synergism and a potent combinational site-specific immunosuppressive drug. The success of CsA/CS therapy would depend on the existence and preservation of CsA's regulatory characteristics and the ability of corticosteroids to function in conjunction with CsA to modulate pre-activated responses.

Animals

In this investigation, male Lewis x Brown Norway $F_1$ rats (LBN, $RT1^{1+N}$) were used as skin donors to male Lewis (LEW $RT1_1$) recipients. The animals weighing around 350 grams were maintained in a temperature controlled environment at the University of California, Irvine vivarium facilities for the duration of the experiments.

Dual Skin Allograft Model

Split thickness donor skin, 0.015 inches in thickness, was taken from the dorsal side of LBN rats with a Gibson Ross dermatome (Thackery Instruments, England). Each graft ($3 \times 4$ $cm^2$) was transplanted onto the dorsal side of the recipient using 3–0 sutures and stay sutures to secure the grafts. Each graft was monitored daily for erythema, hair growth, eschar, exudate and scabs to determine graft status. When fifty percent of the graft was graded to be necrotic tissue, then the allograft was determined to be at a peak of rejection (50% rejection). First sign of rejection was determined based on the initial observation of erythema, continuous hair loss, flakiness and/or scabs without reverting back to previous conditions (1st sign). Full rejection was characterized by complete necrosis of the allograft skin tissue and establishment of scar tissue (full rejection).

Experimental Protocol

Three different protocols were employed to study the mechanisms of site-specific immunosuppression with CsA-HC combinational therapy. All groups received 10 days of systemic CsA (Sandoz oral solution, Sandoz, USA) post-transplantation. Topical (2.5%) CsA was made in a oleaginous base formulation that provided moderate local efficacy (EPIX, Santa Ana, Calif., see below). In regimen 1, 5 mg/Kg/day of CsA was applied topically following the 10 days of systemic CsA treatment until full rejection as described previously. Topical application of a mixture of 2.5% CsA and 1.0% HC following the 10 days systemic treatment was employed for regimen 2. For regimen 3, topical application of 2.5% CsA alone was applied until initial signs of rejection, then was switched to the combinational mixture formulation until full rejection.

Statistical Analysis

Appropriate use of the unpaired and paired Student-T test was employed for all evaluation of data. Survival data was converted to a logarithmic transformation to correct for skewness. P values were considered significant if they were less than 0.05.

CsA provided prolongation of skin allografts in a site-specific manner when applied topically using the dual skin allograft model. In FIG. 2 the survival of placebo treated skin allografts and disparity in survival between experimental and placebo treated grafts are displayed. A base formulation was utilized that provided moderate efficacy with CsA in comparison to previously published formulations (1,2), but was compatible with HC formulation and addition. For each group, a significant disparity between the experimental graft and placebo graft was obtained (p<0.05). The experimental graft appeared normal for the duration of the prolongation phase with full hair growth and normal skin texture. Three different protocols were evaluated: 1) Topical CsA (2.5%) at the induction phase through the entire rejection process; 2) Combined topical CsA/HC (2.5%/1.0%) at the induction phase through the entire rejection process; and 3) Topical CsA during the immune induction phase and subsequent addition of combined CsA/HC at initiation of the maintenance phase to full rejection. Topical CsA provided moderate graft prolongation and disparity (FIG. 2). Mean survival times increased slightly with combined topical CsA/HC in comparison to CsA alone, but, did not provide significant synergism (FIG. 2). However, topical CsA during immune response induction or the antigen-dependent phase with subsequent suppression of antigen-independent inflammation by topical CsA/HC provided dramatic synergism with optimal efficacy and disparity (FIG. 2).

Addition of topical HC in combination with topical CsA at first sign of rejection to an allograft previously treated with topical CsA alone provided the synergistic combinational effect. Prior to the first sign of rejection, the experimental graft of group was similar to the results of groups 1 and 2. However, addition of corticosteroid in combination with CsA after initial signs of rejection reversed the erythema and hair loss associated with rejection in all of the animals in this group. The graft returned to good health with full hair growth in 4 out of 5 animals. Notice that the disparity in group 3 was approximately 3× more than groups 1 or 2. The synergistic effects were expressed only during the maintenance phase of CsA/HC combined treatment during the overlapping of Ag-dependent and Ag-independent mechanisms.

Systemic profiles of serum CsA yielded a predictable trend in placebo treated skin allograft survival (FIG. 3). Ten day subcutaneous treatment reached a peak of 1,700 ng/ml at day 11. Subtherapeutic levels were reached and maintained by day 25. Placebo grafts rejected shortly thereafter, as expected.

These results demonstrate that topical CsA is effective at locally modulating early immune events during the induction phase which can be considered primarily an antigen-dependent process. CS can be considered to primarily inhibit antigen-independent, nonspecific inflammatory reactions. Thus CS may be most effective during recruitment of nonspecific inflammatory components which are less sensitive to CsA. The simultaneous addition of CsA and CS in topical formulations would theoretically enhance immunomodulation since concomitant inhibition of antigen-dependent and antigen-independent responses by these agents, respectively, would be active (Group II). However, significantly enhanced immunomodulation was not observed in this case. Based on the mechanisms of action of both drugs, results suggest that CS may suppress the beneficial expression of CsA induced, immunoregulatory mechanisms. However, these beneficial mechanisms were only expressed with the subsequent addition of antigen-independent inflammatory cascade suppression by CS in combination with CsA (Group 3).

It has been established that corticosteroids down-regulate Major Histocompatibility Complex (MHC) class II expression and destabilize membranes of Antigen Presenting Cell (APC) and/or immunocompetent cells (20). Since antigen recognition has been shown to be important for CsA's mechanism of action and immunosuppressive efficacy (9,10), CS may inhibit CsA immunosuppression by interfering with these early activation events. CS may also abrogate on-going mechanisms of readaptation within the graft. It has been demonstrated the CsA spares or even facilitates suppressor T-cell expression (10). But, the development of, and even the effect of, the suppressor cell network could possibly be abrogated locally by CS addition as shown in other studies (21–23). Also, peripheral selection of the T cell repertoire is dependent on T cell receptor (TCR)-ligand interactions (24). If CS is applied at the beginning of the Ag-dependent immune response induction phase, then peripheral selection of local T cells could be impaired, since CS destabilizes membranes and down regulates receptor interactions (11–14). Therefore, CsA induced clonal deletion mechanisms may not be developed under concomitant CS coverage. However, the deletion of alloresponsive cells during early CsA sensitive phases could act synergistically with Ag-independent suppression when nonspecific inflammatory elements are recruited (initiation of the rejection phase).

A decrease in alloresponsive cells would result in low mediator release and hence low recruitment of non-specific inflammatory elements. Studies performed using infiltrating sponge matrix allograft models demonstrate at the peak of infiltration only 0.2% of the cells were Ag-specific T cytotoxic lymphocytes (25,26). Thus, this implies that the other 99.8% are non-specific inflammatory cells responding to production of immune mediators by the initially small numbers of antigen-specific infiltrating cells. This may also explain the synergistic effect observed in our experiments.

Since the simultaneous administration of CsA and HC during the induction phase did not provide synergistic site specific immunomodulation, we can conclude that the development of regulatory mechanisms induced by CsA at this time are steroid sensitive. However, once these regulatory elements were established, their effects were not steroid sensitive. The results of this study, therefore, suggests that a topical CsA/HC combinational drug or possibly even systemic CsA/HC therapy can be optimally employed with proper timing. This would allow both CsA and HC to result in their most potent effect synergistically on selective cellular and phasic events occurring along the course of antigen-dependent, immune responsiveness, and nonspecific inflammatory responsiveness. Therefore, the timing of corticosteroid addition during immune response induction in combination with CsA should be considered carefully since it may potentially negate the beneficial regulatory mechanisms at critical phases triggered by CsA. Studies are currently in progress using immunohistochemical staining and cell trafficking techniques to further study these mechanisms of action. The application of CS at the first sign of rejection has been used systemically for salvage of CsA treated kidney, liver, and heart grafts in clinical situations (27–31). Similarly, use of CS site-specifically or topically, in combination with CsA has surprising benefits. The optimal therapeutic protocol for combinational therapy of CsA and CS would be suggested to be when nonspecific inflammatory events are initiated following the induction of beneficial CsA immunomodulatory mechanisms.

In conclusion, these results provide further support of our previous findings that local site-specific or systemic efficacy via topical delivery to the skin can be dependent upon carrier composition with particular emphasis on solvent efficiency, the hydrophilic/lipophilic nature of the vehicle, viscosity, active principle solubilization, and concentration.

Topical formulations of cyclosporine and other anti-inflammatory compounds have been successfully developed and tested in animal studies. They have been studied for transdermal penetration and their ability to effect localized anti-inflammatory responses in the skin. Certain principles have been defined, with respect to the vehicle, as important and necessary for efficacy. In addition, dose and timing requirements have been studied and a critical method has been identified for successful treatment. In addition, a novel animal model has been developed to screen anti-inflammatory formulations, their efficacy, toxicity, and mechanisms of action. Systemic application is necessary to modulate the immune response in accord with the known mechanisms of actions of cyclosporine. In addition, as wound healing is expedited with systemic administration, a nidus of inflammation is therefore avoided. In conclusion, it is believed that these findings are directly transferable to other inflammatory reactions including autoimmune diseases of the skin in the clinical realm.

The solubility of the compound and polarity of the carriers appears to influence levels of transdermal drug delivery. Certain non-polar oleaginous hydrophobic/lipophilic carriers, in these instances, enable the lipophilic active principle to penetrate the skin barrier, depot within the tissue in high concentrations, and effect local site-specific immunosuppression. Carriers with an increased polar nature and that are broadly efficient solvents enhance transdermal penetration and therefore, local and systemic effects. It has been proven that such classes of carriers are one of the key factors in achieving transdermal drug delivery and systemic actions. Different formulations can be easily devised to produce creams or ointments which may prove advantageous.

It will be understood that the scope of this invention is not limited by the above-described preferred embodiment. It will be understood that various changes and modifications can be made therein without departing from the spirit and scope of the invention, which are defined by the following claims.

REFERENCES

1. Black K.,s. Hewitt C. W., C. L. C. Chau, and L. Pizzo. "Transdermal Application of Cyclosporine Prolongs Skin Allograft Survival." *Transplant. Proc.* 1988; 20(2):660–662.
2. Black K. S., Nguyen D. K., Procter C. M., Patel M. P., Hewitt C. W. "Site-specific Suppression of Cell-Mediated Immunity by Cyclosporine." *J. Invest. Derm.* 1990; 94(5):644–8
3. Griffiths C. E. M, Powles A. V., Baker B. S. and Valdimarsson H. "Combination of Cyclosporine A and Topical Corticosteroid in the Treatment of Psoriasis." *Transplant. Proc.* 1988; 20(3):50–52.
4. Toyry S., Fraki J. and Tammi R. "Mast Cell Density in Psoriatic Skin. The Effect of PUVA and Corticosteroid Therapy." *Arch. Dermatology* 1988; 280: 282–285.
5. Gorensek M. J., Stewart R. W., Keys T. F., McHenry M. C., Longworth D. L., Rehm S. J., Babiak T. "Decreased Infections In Cardiac Transplant Recipients, on Cyclosporine With Reduced Corticosteroid Use." *Clev. Clin. J. Med.* 1989; 56(7): 690–695.
6. Tamura F., Vogelsang G. B., Reitz B. A., Baumgartner W. A., and Herskowitz A. "Combination Thalidomide and Cyclosporine for Cardiac Allograft Rejection." *Transplantation* 1990; 49(1): 20–25.
7. Hayry P. and Willebrand E. V. "The influence of the Pattern of Inflammation and Administration of Steroids on Class II MHC Antigen Expression in Renal Transplants." *Transplantation* 1986; 42:358–363.
8. Hopt U. J., Erath F., Schareck W., Greger B., Mellert J. "Effect of Cyclosporine A on Local Inflammation in Rejecting Allografts." *Tranplant. Proc.* 1988; 20(2):163–169.
9. Kahan B. D. "Cyclosporine: The Agent and Its Actions." *Transplant. Proc.* 1985; 17(4): 5–18.
10. Hess A. D., Tutschka P. J. "Effect of Cyclosporine A on Human Lymphocyte Response In Vitro." *J. Immunonol.* 1980; 124(6): 2601–2608.
11. Boss P. S., Jolley W. B. and Ainsworth E. J. "Mechanisms of Action of Topically Applied Triamcinolone Acetonide in Prolonging Skin Allograft Survival Time." *Transplant. Proc.* 1988; 15(1): 17–21.
12. Ashworth J., Booker J. and Breathnach S. M. "Effects of Topical Corticosteroid Therapy on Langerhans Cell Antigen Presenting Function in Human Skin." *Dermatology* 1988; 118:457–470.
13. Takeda K., Arase S. and Takahashi S. "Side Effects of Topical Corticosteroids and Their Prevention." *Drugs* 1988; 36:15–23.
14. Topert M. "Perspectives in Corticosteroid Research." *Drugs* 1988; 36:1–8.
15. Sanders, M. E., Makgoba, M. W., Sharrow, S. O., Stephany, D., Springer, T. A., Young, H. A. and Shaw, S. "Human Memory T Lymphocytes Express Increased Levels of Three Cell Adhesion Molecules (LFA-3, CD2, and LFA-1) and Three Other Molecules (UCHL-1, CDw29, and Pgp-1) and Have Enhanced IFN-Gamma Production." *J. Immunol.* 1988 140:1401–7.
16. Budd, R. C., Cerottini, J. C., and MacDonald, H. R. "Selectively Increased Production of Interferon by Subsets of Lyt-2+ and L3T4+ T Cells Identified by Expression of Pgp-1. " *J. Immunol.* 1987; 138:3583–86.
17. Arthur, R. P., Mason, D. "T Cells That Help B Cell Responses to Soluble Antigen Are Distinguishedable From Those Producing Interleukin-2 on Mitogenic or Allogenic Stimulation." *J. Exp. Med.* 1986; 163:774–86.
18. Swain, S. L., Weinberg, A. D., English M. "CD4+ T Cell Subsets. Lymphokine Secretion of Memory Cells and of Effector Cells That Develop From Precursors In Vitro." *J. Immunol.* 1990; 144:1788–99.
19. Lee, W. T., Yin, X. M., Vitetta, E. S. "Analysis of Murine CD45 R High and CD45 Low CD4+ T cells." *J. Immunol.* 1990; 144:3288–95.
20. Mellert, J., Hopt, U. T., Erath, F., Holzer, H. "Differential Effects of Azathioprine (Aza), Cyclosporine A (CsA) and Dexamethaxone (Dexa) on Lymphokine Mediated Inflammation in Rejecting Allografts." *Transplant. Proc.* 1989; 21: 98–9.
21. Ikeda T, Urchihara M, Daiguji Y, Hasumura Y, and Takeuchi J. "Immunological Mechanisms of Corticosteroid Therapy in Chronic Active Hepatitis: Analysis of Peripheral Blood Suppressor T-cell and Interleukin 2 Activities." *Clin. Immunol. Immunopathol.* 1989; 53(2 pt 1):192–201.
22. Ikeda T. Daiguji Y. Hasumura Y. and Takeuchi J. "In Vitro Effect of Prednisolone on Peripheral Blood Suppressor T Cell Activity in Patients With Alcoholic Hepatitis." *Clin. Immunol. Immunopathol.* 1989; 53:225–32.
23. Highet A. B. and Ruben Ln. "Corticosteroid Regulation of IL-1 Production May Be Responsible for Deficient Immune Suppressor Function During the Metamorphosis of *Xenopus Laevis*, the South African Clawed Toad." *Immunnol. Pharm.* 1987 13:149–55.
24. Rocha B. and Boehmer H. V. "Peripheral Selection of the T Cell Repertoire. *Science* 1991; 251:1225–28.
25. Orosz C. G., Zinn N. E., Sirinek L., Ferguson R. M. "In Vivo Mechanisms of Alloreactivity. Frequency of Donor Reactive Cytotoxic T Lymphocytes in Sponge-Matrix Allografts." *Transplantation* 1986; 41: 75–83.
26. Orosz C. G., Zinn N. E., Sirinek L., Ferguson R. M. "In Vivo Mechanisms of Alloreactivity. Allospecificity of Cytotoxic T Lymphocytes in Sponge Matrix Allografts as Determined by Limiting Dilution Analysis." *Transplantation* 1986; 41(1): 84–92.
27. Halasz N. A., Gamboa E. A., Ward D. M., Steiner R. W., and Bronsther. "Kidney Transplantation in the CsA Era." *Arch. Surg.* 1987; 122:1001–1004.
28. Novick A. C., Ho-Hsieh H., Steinmuller D., Streem S. B., Cunningham R. J., Steinhilber D., Coormastic M., and Buszta C. "Detrimental Effect of Cyclosporine on Initial Function of Cadaver Renal Allografts Following Extended Preservation." *Transplantation* 1986; 42:154–158.
29. Veremis S. A., Maddux M. S., Pollak R., Kline S. S., and Mozes M. F. "Alternative Antirejection Treatment With Steroids or Antilymphoblast Gobulin in Renal Transplant Patients Receiving Cyclosporine." *Tranplant. Proc.* 1987; 19:1893–1895.
30. Tilney N. L., Milford E. L., Araujo J. L., Strom T. B., Carpenter C. B. Kirkman R. L. "Experience with Cyclosporine and Steroids in Clinical Renal Transplantation. *Ann. Surg.* 1984; 200:605–613.
31. Najarian J. S., Fryd D. S., Strand M., Canafax D. M., Ascher N. L., Payne W. D., Simmons R., Sutherland D. E. R. *Ann. Surg.* 1985; 201:142–157.

It will be understood that the scope of this invention is not limited by the design of the above described preferred embodiment. While the invention is described and taught using the preferred embodiment, it will be understood that various changes and modifications can be made therein without departing from the spirit and scope of the invention, which are defined by the following claims.

We claim

1. A pharmaceutical composition comprising in approximate amounts by weight:
   a. 5–60% anhydrous lanolin;
   b. 5–80% jojoba oil;
   c. 5–80% olive oil;
   d. 0.2–20% polysorbate 80; and
   e. 0.2–25% cyclosporine.

2. A pharmaceutical composition comprising in approximate amounts by weight:
   a. 5–60% anhydrous lanolin;
   b. 5–80% mineral oil;
   c. 5–80% olive oil;
   d. 0.2–20% polysorbate 80; and
   e. 0.2–25% cyclosporine.

3. A pharmaceutical composition comprising in approximate amounts by weight:
   a. 5–60% anhydrous lanolin;
   b. 5–80% white petrolatum;
   c. 5–80% olive oil;
   d. 0.2–20% polysorbate 80; and
   e. 0.2–25% cyclosporine.

4. The pharmaceutical composition of claim 1, further comprising an effective amount of one or more immunosuppressants selected from the group consisting of: tacrolimus, mizoribine, azathioprine, cyclophosphamide, deoxyspergualin, didemnin B, methotrexate, thalidomide, rapamycin, or combinations thereof.

5. The pharmaceutical composition of claim 2, further comprising an effective amount of one or more immunosuppressants selected from the group consisting of: tacrolimus, mizoribine, azathioprine, cyclophosphamide, deoxyspergualin, didemnin B, methotrexate, thalidomide, rapamycin, or combinations thereof.

6. The pharmaceutical composition of claim 3, further comprising an effective amount of one or more immunosuppressants selected from the group consisting of: tacrolimus, mizoribine, azathioprine, cyclophosphamide, deoxyspergualin, didemnin B, methotrexate, thalidomide, rapamycin, or combinations thereof.

7. The pharmaceutical composition of claim 1, further comprising in approximate amounts by weight between 0.05–5% of hydrocortisone powder.

8. The pharmaceutical composition of claim 2, further comprising in approximate amounts by weight between 0.05–5% of hydrocortisone powder.

9. The pharmaceutical composition of claim 3, further comprising in approximate amounts by weight between 0.05–5% of hydrocortisone powder.

* * * * *